(12) United States Patent
Emde et al.

(10) Patent No.: US 8,278,454 B2
(45) Date of Patent: Oct. 2, 2012

(54) PROCESS FOR PREPARING TETRAHYDROQUINOLINE DERIVATIVES

(75) Inventors: Ulrich Emde, Darmstadt (DE); Oliver Block, Rossdorf (DE); Kai Schiemann, Seeheim-Jugenheim (DE)

(73) Assignee: Merck Patent Gesellschaft mit beschränkter Haftung, Darmstadt (DE)

( * ) Notice: Subject to any disclaimer, the term of this patent is extended or adjusted under 35 U.S.C. 154(b) by 161 days.

(21) Appl. No.: 12/808,819

(22) PCT Filed: Nov. 20, 2008

(86) PCT No.: PCT/EP2008/009805
§ 371 (c)(1),
(2), (4) Date: Jun. 17, 2010

(87) PCT Pub. No.: WO2009/077052
PCT Pub. Date: Jun. 25, 2009

(65) Prior Publication Data
US 2010/0311976 A1    Dec. 9, 2010

(30) Foreign Application Priority Data

Dec. 18, 2007    (EP) .................................. 07024509

(51) Int. Cl.
*C07D 401/00*    (2006.01)

(52) U.S. Cl. ........................................................ 546/196
(58) Field of Classification Search .................. None
See application file for complete search history.

(56) References Cited

U.S. PATENT DOCUMENTS 7,868,172 B2 *   1/2011   Schiemann et al. ............ 546/80

FOREIGN PATENT DOCUMENTS

| WO | 2005063735 A1 | 7/2005 |
| WO | PCTEP0809805 R | 6/2009 |

OTHER PUBLICATIONS

Vippagunta, S. et al., 2001, Adv. Drug Deliv. Rev. vol. 48, pp. 3-26.*
Jahangiri, G et al., J. Amer. Chem. Soc. 1994 vol. 116 pp. 11264-11274.*

* cited by examiner

*Primary Examiner* — Janet Andres
*Assistant Examiner* — Heidi Reese
(74) *Attorney, Agent, or Firm* — Millen, White, Zelano & Branigan, P.C.

(57) ABSTRACT

The invention relates to a novel process for preparing enantiomerically enriched or pure tetrahydroquinoline derivatives by reacting a chiral dihydropyran-methylamine C with a aldehyde B and an aniline A in a multicomponent one pot synthesis in the presence of a protonic acid or lewis acid with a suitable solvent. A, B, C have the meaning as described in the specification.

23 Claims, No Drawings

PROCESS FOR PREPARING TETRAHYDROQUINOLINE DERIVATIVES

The invention relates to a process for the manufacture of enantiomerically enriched or pure compounds of formula I:

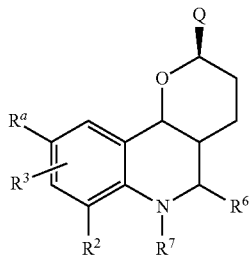

$R^a$ denotes Hal, cyano, COOH, COOA, A, $CF_3$;
$R^1$ denotes H, A, Aryl, Het, Hal, —$(CY_2)_n$—SA, —$(CY_2)_n$—$SCF_3$, —$(CY_2)_n$—SCN, —$(CY_2)_n$—$CF_3$, —$(CY_2)_n$—$OCF_3$, R, cycloalkyl, —$SCH_3$, —SCN, —$CF_3$, —$OCF_3$, —OA, —$(CY_2)_n$—$CO_2R$, —$(CY_2)_n$—CN, —$(CY_2)_n$-Hal, —$(CY_2)_n$—$NR_2$, —$(CY_2)_n$—OA, —$(CY_2)_n$—OCOA, —$SCF_3$, —$(CY_2)_n$—$CONR_2$, —$(CY_2)_n$—NHCOA, —$(CY_2)_n$—$NHSO_2A$, $SF_5$, $Si(CH_3)_3$, CO—$(CY_2)_n$—$CH_3$, —$(CY_2)_n$—N— Pyrolidon, $(CH_2)_n$NRCOOR, NRCOOR, NCO, $(CH_2)_n$COOR, NCOOR, $(CH_2)_n$OH, $NR(CH_2)_nNR_2$, $C(OH)R_2$, $NR(CH_2)_nOR$, NCOR, $(CH_2)_nAr$, $(CH_2)_n$Het, $(CH_2)_nR^1$, $(CH_2)_nX(CH_2)_nAr$, $(CH_2)_nX(CH_2)_n$Het, $(CH_2)_nCONR_2$, $XCONR(CH_2)_nNR_2$, $N[(CH_2)_nXCOOR]CO(CH_2)_nAr$, $N[(CH_2)_nXR]CO(CH_2)_nAr$, $N[(CH_2)_nXR]CO(CH_2)_nXAryl$, $N[(CH_2)_nXR]SO_2(CH_2)_nAr$, $N[(CH_2)_nNR-COOR]CO(CH_2)_nAr$, $N[(CH_2)_nNR_2]CO(CH_2)_nAr$, $N[(CH_2)_nNR_2]CO(CH_2)_nNRAr$, $N[(CH_2)_nNR_2]SO_2(CH_2)_nAr$, $N[(CH_2)_nXR]CO(CH_2)_n$Het, $N[(CH_2)_nXR]CO(CH_2)_nX$-Het, $N[(CH_2)_nXR]SO_2(CH_2)_n$Het, $N[(CH_2)_nNRCOOR]CO(CH_2)_n$Het, $N[(CH_2)_nNR_2]CO(CH_2)_n$Het, $N[(CH_2)_nNR_2]CO(CH_2)_n$NRHet;

$R^2$, $R^3$ denotes H, A, Hal, OA, OR;
Y denotes H, A, Hal, OR;
A denotes Alkyl or Cycloalkyl, wherein one or more H-atoms can be replaced by Hal;
Hal denotes F, Cl, Br or I;
R denotes H or A, in the case of geminal groups R together also —$(CH_2)_5$—, —$(CH_2)_4$— or —$(CH_2)_n$—X—$(CH_2)_n$, or —$(CH_2)_n$—Z—$(CH_2)_n$;
X denotes O, S or $NR^1$;
Q denotes $CH_2$—NH-A, $CH_2$—NH—$C(O)R^1$, $CH_2$—NH—$SO_2R^1$;
Z denotes $CH_2$, X, $CHCONH_2$, $CH(CH_2)_nNR^1COOR^1$, $CHNR^1COOR^1$, NCHO, $CHCON(R^1)_2$, $CH(CH_2)_nCOOR^1$, $NCOOR^1$, $CH(CH_2)_nOH$, $N(CH_2)_nOH$, $CHNH_2$, $CH(CH_2)_nNR^1_2$, $CH(CH_2)_nNR^1_2$, $C(OH)R^1$, $CHNCOR^1$, $NCOR^1$, $N(CH_2)_nAr$, $N(CH_2)_n$Het, $CHR^1$, $NR^1$, $CH(CH_2)_nAr$, $CH(CH_2)_n$Het, $CH(CH_2)_nR^1$, $N(CH_2)_nCOOR^1$, $CH(CH_2)_nX(CH_2)_nAr$, $CH(CH_2)_nX(CH_2)_n$Het, $N(CH_2)_nCON(R^1)_2$, $NSO_2R^1$, $CHSO_2N(R^1)_2$, $XCONR(CH_2)_nN(R^1)_2$, $NCO(CH_2)_nAr$, $NCO(CH_2)_nXAr$, $NSO_2(CH_2)_nAr$, $NCO(CH_2)_nAr$, $NCO(CH_2)_nNR^1Aryl$, $NCO(CH_2)_n$Het, $NCO(CH_2)_nX$-Het, $NSO_2(CH_2)_n$Het, $NCO(CH_2)_nNR^1$Het, $N(CH_2)_nNR_2CH$, $CHO(CH_2)_nN(R^1)_2$, $CHX(CH_2)_nN(R^1)_2$, $NCO(CH_2)_nNR_2$;

$R^6$ denotes unsubstituted Ar or Het which is substituted in at least one position by Hal, $NO_2$, CN, OR, A, —$(CY_2)_n$—OR, —OCOR, —$(CY_2)_n$—$CO_2R$, —$(CY_2)_2)_n$—CN, —NCOR, —COR or —$(CY_2)_n$—$NR_2$ or by Aryl or Het which also may be substituted by Hal, $NO_2$, CN, A, OR, OCOR, COR, $NR_2$, $CF_3$, $OCF_3$, $OCH(CF_3)_2$, $R^7$ denotes (C=O)—R, (C=O)—$NR_2$, (C=O)—OR, H or A;

Ar denotes a monocyclic or bicyclic, saturated, unsaturated or aromatic carbocyclic ring having 6 to 14 carbon atoms which may be unsubstituted which is substituted in at least one position by Hal, $NO_2$, CN, OR, A, —$(CY_2)_n$—OR, —OCOR, —$(CY_2)_n$—$CO_2R$, —$(CY_2)_n$—CN, —NCOR, —COR or —$(CY_2)_n$—$NR_2$ or by Hal, $NO_2$, CN, A, OR, OCOR, COR, $NR_2$, $CF_3$, $OCF_3$, $OCH(CF_3)_2$;

Het denotes a monocyclic or bicyclic, saturated, unsaturated or aromatic heterocyclic ring having 1 to 4 N, O and/or S atoms which may be unsubstituted or which is substituted in at least one position by Hal, $NO_2$, CN, OR, A, —$(CY_2)_n$—OR, —OCOR, —$(CY_2)_n$—$CO_2R$, —$(CY_2)_n$—CN, —NCOR, —COR or —$(CY_2)_n$—$NR_2$ or by Hal, $NO_2$, CN, A, OR, OCOR, COR, $NR_2$, $CF_3$, $OCF_3$, $OCH(CF_3)_2$;

n denotes 0, 1, 2, 3, 4, 5, 6 or 7;

as well as their pharmaceutically acceptable derivatives, solvates, tautomers, salts and polymorphic forms.

Processes according to the invention are relating to the manufacture of enantiomerically enriched or pure compounds of formula Ia

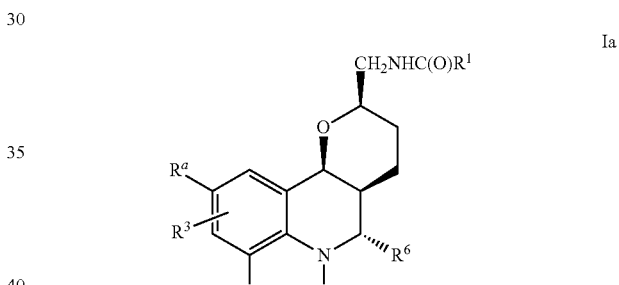

wherein $R^1$ to $R^7$ has the meaning given above and $R^a$ is Hal, cyano, COOH, COOA or A.

Most preferred processes according to the invention are relating to the manufacture of enantiomerically enriched or pure compounds of formula Ia1

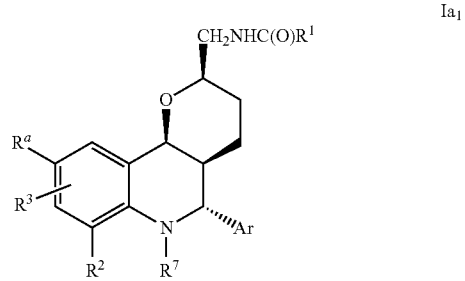

wherein $R^1$ to $R^7$, Ar has the meaning given above and $R^a$ is Hal, cyano, COOH, COOA or A.

Very most preferred processes according to the invention are relating to the manufacture of enantiomerically enriched or pure compounds formula $Ia_2$:

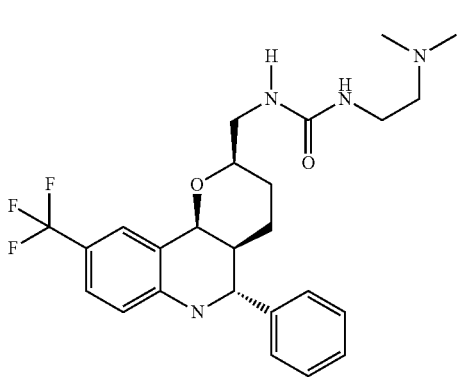

Ia₂

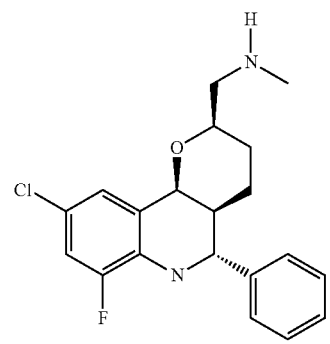

Ib₂

(1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea) is obtained by the inventive process.

Processes according to the invention are relating to the manufacture of enantiomerically enriched or pure enantiomers of formula Ib

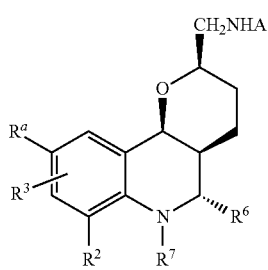

Ib₁ wherein $R^1$ to $R^7$ has the meaning given above and $R^a$ is Hal, cyano, COOH, COOA or A.

Most preferred processes according to the invention are relating to the manufacture of enantiomerically enriched or pure compounds of formula Ib₁

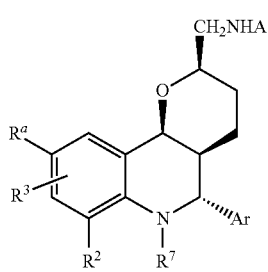

Ib₁ wherein $R^1$ to $R^7$, Ar has the meaning given above and $R^a$ is Hal, cyano, COOH, COOA or A.

Very most preferred Processes according to the invention are relating to the manufacture of enantiomerically enriched or pure compounds of formula Ib₂:

((2R,4aS,5R,10bS)-9-Chloro-7-fluoro-5-phenyl-3,4,4a,5,6,10b-hexahydro-2H-pyrano[3,2-c]quinolin-2-ylmethyl)-methyl-amine.

The invention relates also to compound of formula C and their enantiomerically enriched or pure enantiomers:

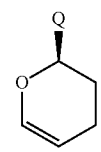

C wherein C is as described above as well as their pharmaceutically acceptable derivatives, solvates, tautomers, salts and polymorphic forms.

The invention relates also to compound of formula C' and their enantiomerically enriched or pure enantiomers:

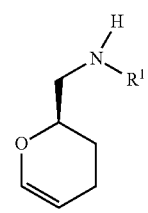

C' wherein $R^1$ is as described above as well as their pharmaceutically acceptable derivatives, solvates, tautomers, salts and polymorphic forms.

The invention relates also to a process for the manufacture of pure enantiomers compounds of formula C:

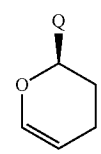

C wherein Q denotes $CH_2$—NH—A, $CH_2$—NH—C(O)$R^1$, $CH_2$—NH—SO₂$R^1$ and $R^1$ is as described above as well as their pharmaceutically acceptable derivatives, solvates, tautomers, salts and polymorphic forms.

The invention relates also to a process for the manufacture of pure enantiomers compounds of formula C':

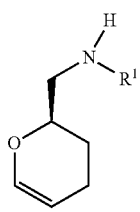

C' wherein $R^1$ is as described above as well as their pharmaceutically acceptable derivatives, solvates, tautomers, salts and polymorphic forms.

The term enantiomerically enriched or pure preferably refers to an enantiomeric purity of above 60%, such as about 80% to about 100%. Especially the term refers to an enantiomeric purity of higher than about 98%.

The compound of formula I as well as therapeutically acceptable salts thereof, are described in WO 2005/063735.

The compound of formula I is therapeutically active and especially useful in the treatment of proliferative diseases.

The phenyl-hexahydro-2H-pyranoquinolin core of the compounds of formula I can be obtained by aza-Diels-Alder reaction (see Magesh et al. *Bioorganic & Medicinal Chemistry Letters* 14 (2004) 2035-2040, Yadav et a. *Tetrahedron* 59 (2003), 1599-1604) or by reaction of a dihydropyran moiety with a benzaldehyde moiety in a presence of an aniline derivative and $SOCl_2$ (see Biswanath et al. Journal of Chemical Research, (12), 793-795 (2005). The synthesis can be also carried out by reacting an aniline derivative with a benzaldehyde group in the presence of vinyl derivatives as described in WO2005063735. This synthesis relates to compounds, wherein the dihydropyran moiety used is not substituted and also not chiral. It has been shown that hexahydro-2H-pyranoquinolin derivatives (family of tetrahydroquinolines, THQ's) and, especially Phenyl-hexahydro-2H-pyranoquinolin-2-methylamines are potent inhibitors of kinesin Eg5 (WO2005063735). It has also be shown that an enantiopure or enantiomerically enriched form of the drug shows improved activity against the biological target. Compounds containing a THQ core display proven strong mutagenic, carcinogenic and conjecturally teratogenic effects on living organisms and mammals. Moreover, as the compounds are Eg5 kinesin inhibitors they interact directly with the cell division cycle of living organisms. Consequently, THQ amines have to be classified as highly potent and cytotoxic compounds and during the THQ amine production, shipping and handling special and expensive safety measures have to be installed. A new synthesis route towards enantiopure THQ amines, in which the THQ core is installed in one of the later synthesis steps, preferably the last synthesis step, would help to decrease these special safety measures significantly. The present invention provides a new synthetic route that provides enantiomerically enriched or pure forms of compounds of formula I from a respective enantiomerically enriched or pure chiral dihydropyran methyl amine derivative in a one pot synthesis in the presence of aniline and benzaldehyde derivative. The present invention also provides an advantageous synthetic route that will minimize safety measures and costs considerably. The invention provides also new pure stereoisomers of dihydropyran methylamine derivatives.

The compounds of the present invention are used for the treatment and prophylaxis of diseases that are influenced by inhibition, regulation and/or modulation of the mitotic motor proteins, especially the mitotic motor protein Eg5. These are predominantly all types of cancer and other neoplastic diseases.

The compounds of the formula I and salts thereof are obtained by the following process, characterised in that a compound of formula A

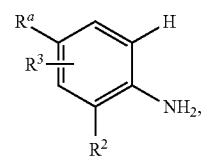

A in which $R^1$, $R^2$ and $R^3$ have the meanings indicated above, is reacted with a compound of the formula B

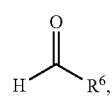

B in which
$R^6$ has the meaning indicated above,
and with a compound of the formula C,

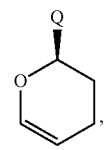

C wherein Q is described above,

More preferably the compounds of the formula I and salts thereof are obtained by the following process, characterised in that a compound of formula A

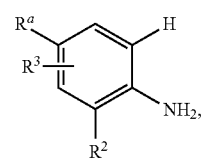

A in which $R^1$, $R^2$ and $R^3$ have the meanings indicated above, is reacted with a compound of the formula B

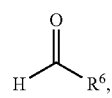

B in which $R^6$ has the meaning indicated above,
and with a dihydropyran methylamine derivative of the formula C',

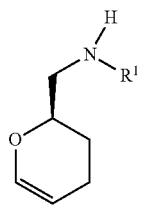

wherein $R^1$ is as defined above. Preferably the reactions are carried out in the presence of a suitable solvent, preferably acetonitrile and a protonic acid or Lewis acid, such as, for example, trifluoroacetic acid, hexafluoroisopropanol, bismuth(III) chloride, ytterbium(III) triflate, scandium(III) triflate or cerium(IV) ammonium nitrate, preferably trifluoroacetic acid. The amino derivatives and preferably the compounds of formula I, wherein Q is $CH_2NH_2$, are may be further transformed into the other compounds of formula I by known procedures, such as alkylation, or acylation.

More surprisingly, it has been found that any acid addition salt of the amino-didropyrane C' or the compound of formula C can be directly applied to the synthesis of the compounds of formula I instead of the free base first, in order to obtain compounds according to formula I. This advantage avoid tedious filtration steps.

Preferred chiral salt of compound related to formula C and C' are L-tosylproline or benzoyl tartaric acid salts and especially (2R,3R)-(−)-Di-O-benzoyl tartaric acid salts, more preferably the salt is L-tosylprolinate.

Above and below, the radicals $R^a$, $R^1$, $R^2$, $R^3$, $R^6$, $R^7$, X, Y, Q, Z, and n have the meanings indicated for the formula I, unless expressly indicated otherwise. If individual radicals occur a number of times within a compound, the radicals adopt the meanings indicated, independently of one another.

A denotes alkyl, is preferably unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. A also denotes cycloalkyl.

Cycloalkyl preferably denotes cyclopropyl, cyclobutyl, cyclopentyl, cyclohexyl or cycloheptyl, but in particular cyclopentyl.

$R^a$ preferably denotes A, Hal. In particular $R^a$ preferably denotes tert-butyl, isopropyl, $CF_3$, Cl or Br.

$R^1$ preferably denotes A, $CF_3$, $OCF_3$, SA, SCN, $CH_2CN$, —OCOA, Hal, $SCF_3$, preferably also t-butyl, —$CH(CH_3)$ $CH_2CH_3$, isopropyl, ethyl or methyl. In particular, $R^1$ denotes t-butyl, isopropyl, ethyl, $CF_3$, methyl, Br, Cl, $SCF_3$, $CH(CH_3)$ $CH_2CH_3$, n-propyl, $OCH_3$, $SCH_3$, n-butyl, —SCN, $CH_2CN$. $R^1$ particularly preferably denotes t-butyl, isopropyl, ethyl or $CF_3$.

$R^2$ preferably denotes H, Hal, A or OA, in particular Br, cyclopropyl, $OCH_3$. Particular preference is furthermore given to H or F.

$R^3$ preferably denotes H or A, in particular H. $R^3$ is preferably in the 5-position. In particular, $R^3$ denotes H or F.

If the radicals and indices, such as, for example, n, occur more than once, the radicals and indices may, independently of one another, adopt different values.

$R^6$ preferably denotes phenyl, 2-, 3- or 4-pyridyl, pyrimidyl, furyl or thienyl, each of which is unsubstituted or mono- or polysubstituted by Hal, CN, $NO_2$, OH, $CF_3$, $OCH(CF_3)_2$, $OCOCH_3$ or A. $R^6$ is preferably not a heteroaromatic radical. In particular, $R^6$ denotes unsubstituted phenyl or one of the following groups:

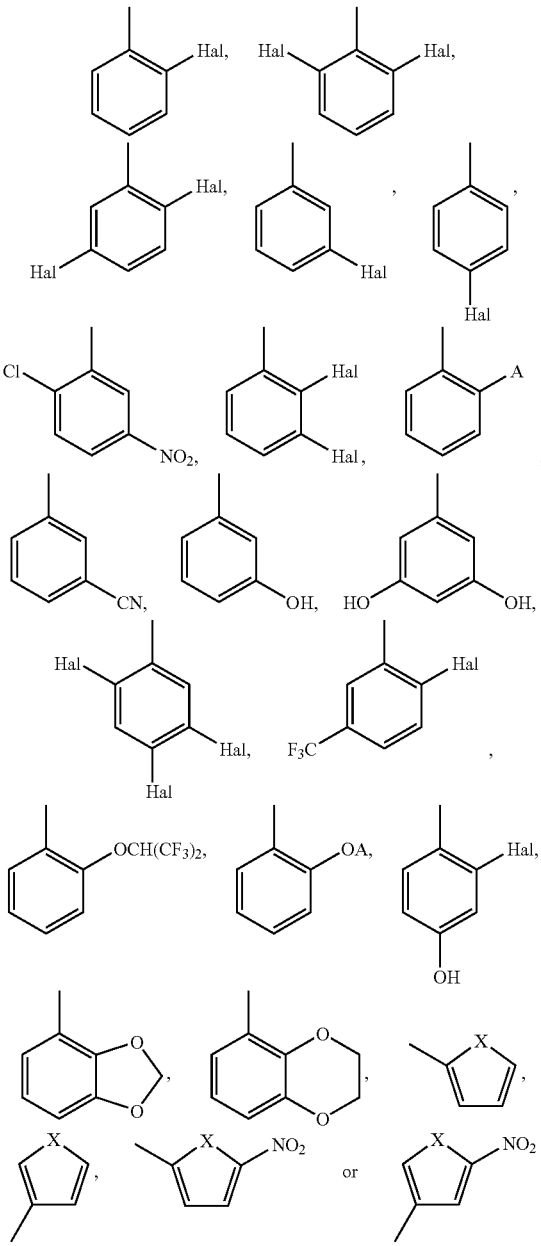

in which
X denotes O, S or NR and in particular O or S, A has the meaning indicated above, but preferably denotes methyl, and Hal preferably denotes F or Cl.

Particular preference is furthermore given to compounds of the formula I in which $R^6$ has one of the following meanings:

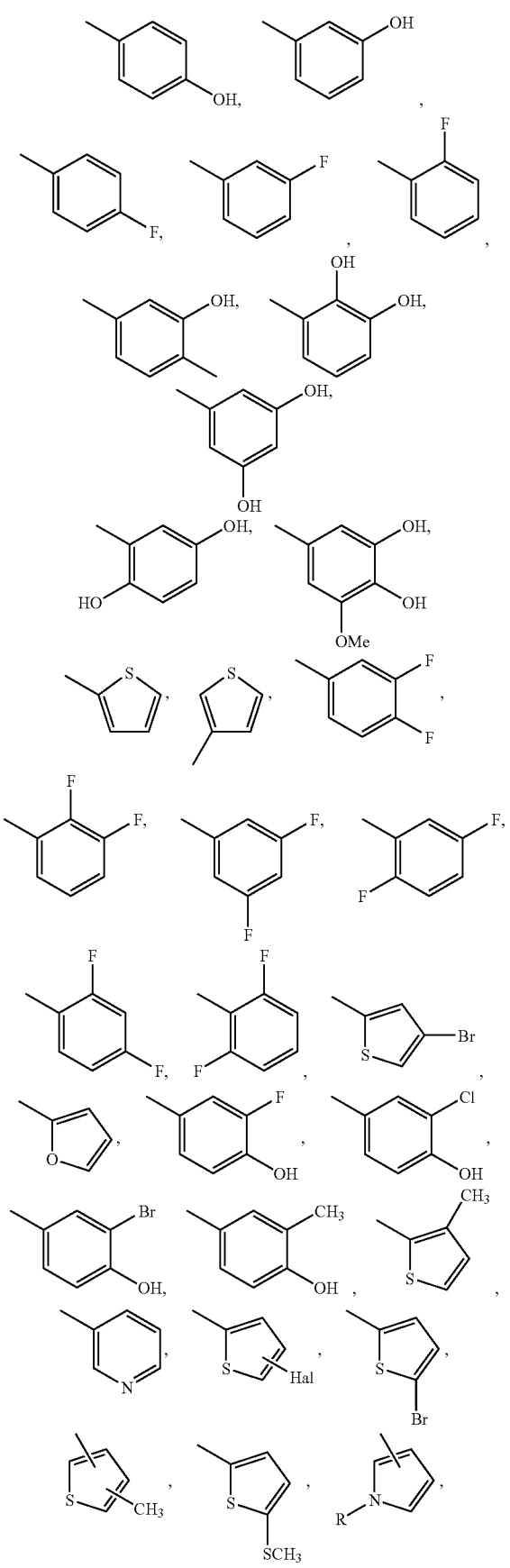

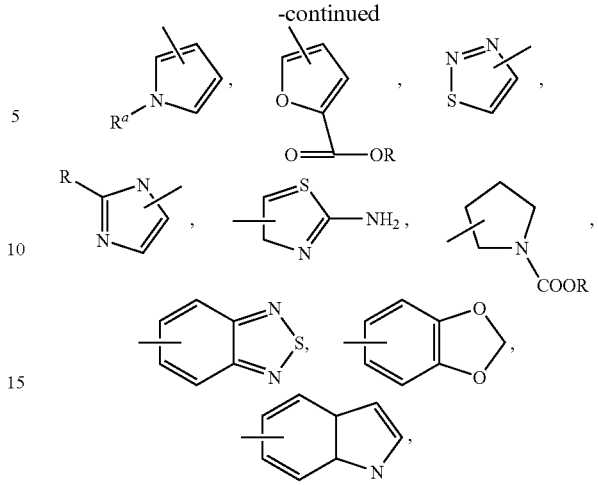

R[7] preferably denotes H or A, in particular H.

Aryl preferably denotes phenyl, naphthyl or biphenyl, each of which is unsubstituted or mono-, di- or trisubstituted by Hal, A, OH, OA, $NH_2$, $NO_2$, CN, COOH, COOA, $CONH_2$, NHCOA, $NHCONH_2$, $NHSO_2A$, CHO, COA, $SO_2NH_2$, $SO_2A$, —$CH_2$—COOH or —$OCH_2$—COOH.

Aryl preferably denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-methoxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3, 5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Heteroaryl preferably denotes a mono- or bicyclic aromatic heterocycle having one or more N, O and/or S atoms which is unsubstituted or mono-, di- or trisubstituted by Hal, A, $NO_2$, NHA, $NA_2$, OA, COOA or CN.

Heteroaryl particularly preferably denotes a monocyclic saturated or aromatic heterocycle having one N, S or O atom, which may be unsubstituted or mono-, di- or trisubstituted by Hal, A, NHA, $NA_2$, $NO_2$, COOA or benzyl.

Irrespective of further substitutions, unsubstituted heteroaryl denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

Hal preferably denotes F, Cl or Br, but also I, particularly preferably F or Cl.

Throughout the invention, all radicals which occur more than once may be identical or different, i.e. are independent of one another.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry] 1992, Georg-Thieme-Verlag, Stuttgart), to be precise under reaction conditions which are known and suitable for the said reactions. Use may also be made here of variants known per se which are not mentioned here in greater detail.

If desired, the starting materials may also be formed in situ so that they are not isolated from the reaction mixture, but instead are immediately converted further into the compounds of the formula I.

The reaction is generally carried out in an inert solvent, preferably in the presence of a protonic acid or Lewis acid, such as TFA, HFIP, bismuth(III) salts, ytterbium(III) salts or CAN. Depending on the conditions used, the reaction time is between a few minutes and 14 days, the reaction temperature is between about 0° and 180°, normally between 0° and 100°, particularly preferably between 15° and 35° C.

Suitable inert solvents are, for example: hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; nitriles, such as acetonitrile; carbon disulfide; carboxylic acids, such as formic acid or acetic acid; nitro compounds, such as nitromethane or nitrobenzene, or mixtures of the said solvents.

Compounds of the formula I in which $R^7$ has a meaning other than H are preferably prepared by alkylation or acylation from the compounds of the formula I in which $R^7$ denotes H.

If desired, a functionally modified amino and/or hydroxyl group in a compound of the formula I can be liberated by solvolysis or hydrogenolysis by conventional methods. This can be carried out, for example, using NaOH or KOH in water, water/THF or water/dioxane at temperatures between 0 and 100°.

The reduction of an ester to the aldehyde or alcohol or the reduction of a nitrile to the aldehyde or amine is carried out by methods as are known to the person skilled in the art and are described in standard works of organic chemistry.

The examples and processes as described which follow will further illustrate the preparation of the compounds of the invention but are not intended to limit the scope of the invention as defined hereinabove or as claimed below.

In a preferred embodiment, the invention relates to compound of formula C and their enantiomerically enriched or pure enantiomers:

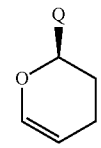

C wherein Q is as described above as well as their pharmaceutically acceptable derivatives, solvates, tautomers, salts and polymorphic forms.

In a very most preferred embodiment the invention relates to compounds according to formula C wherein Q is, $-CH_2-NHA$, $-CH_2-NHR^1$, more preferably $-CH_2$-Me or $-CH_2-NH-CONH-CH_2-CH_2-N(Me)_2$.

In a preferred embodiment the invention relates also to compound of formula C' and their enantiomerically enriched or pure enantiomers:

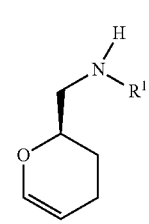

C' wherein $R^1$ is as described above as well as their pharmaceutically acceptable derivatives, solvates, tautomers, salts and polymorphic forms.

In a very most preferred embodiment the invention relates to compounds according to formula C' wherein $R^1$ is Me or $-CONH-CH_2-CH_2-N(Me)_2$.

In a preferred embodiment, the invention relates to a process for the manufacture of enantiomerically enriched or pure compounds of formula C:

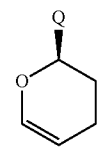

C wherein Q is $CH_2-NH_A$, more preferably $CH_2-NH_2$ as well as its pharmaceutically acceptable derivatives, solvates, tautomers, salts and polymorphic forms comprising the following steps:

a) reacting 3,4-dihydro-2H-pyran-2-carbaldehyde with ammonia or a primary alkylamine, such as methylamine in presence of a catalyst and hydrogen to give the corresponding racemic amine, and preferably dihydropyran methylamine salts;

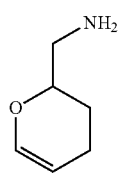

Dihydropyranmethylamine b) treating the racemic amine with a chiral acid compound in a polar solvent to give the pure enantiomeric amine salts, and preferably dihydropyran methylamine salts;
c) optionally treating the amine, and preferably the dihydropyran(DHP) methylamine with a base to obtain compound C in form of a free base.

In a preferred embodiment, the invention relates to a process for the synthesis of compounds according to formula I which starts with commercially available DHP-aldehyde (DHPA) which is allowed to react with ammonia or various primary amines, such as alkylamines, preferably methyl amine. Under Raney-Co catalysis in a suitable solvent such as THF in presence of hydrogen a racemic DHP-alkylamine and preferably DHP-methylamine is formed (See patent DE1233411), as show below.

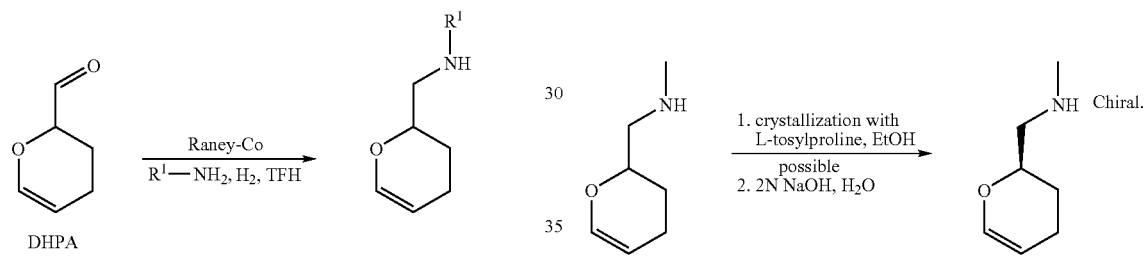

wherein $R^1$ is as described above, more preferably $R^1$ is H, $CH_3$, alkyl, Aryl or Heteroaryl.

In a preferred embodiment the racemic DHP-methylamine is allowed to cristallize with a variety of chiral acids in different solvents to give enantiomerically enriched DHP-alkylamine and preferably DHP-methylamine of formula C'.

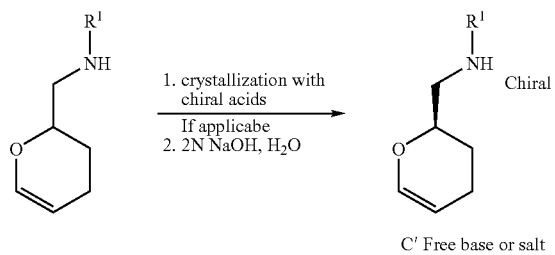

Chiral acids used in this step are preferably tartaric chiral acids or proline, most preferably tartaric chiral acid is (2R,3R)-(−)-di-O-benzoyl tartaric acid, and proline is L-tosylproline.

In a preferred embodiment resolution of primary amine according to formula C and/or C' will take place with chiral proline derivatives, especially with L-tosylproline.

In a preferred embodiment resolution of secondary amine according to formula C and/or C' will take place with tartaric chiral acid, especially with (2R,3R)-(−)-di-O-benzoyl tartaric acid.

Surprisingly, it was found that for subsequent reactions compounds of formula C' can be used in form of L-tosyl proline salt or as free base. In order to obtain the free base of compounds of formula C', the chiral enantiomerically enriched or pure salt, preferably the L-tosyl proline salt of the amine needs to be treated with a strong base such as NaOH preferably 2N NaOH.

Experimental:

It is found for mixtures of compounds of formula C' wherein $R^1$ is methyl, and its antipode that the treatment with equimolar amounts of L-tosylproline in ethanol preferably leads to crystals with the (R)-configured DHP-methylamine. The enantiomeric purity was determined by chiral HPLC to be er=93:7 for the desired (R)-DHP-methylamine enantiomer. Recrystallization from ethanol provided the (R)-DHP-methylamine (as L-tosyl proline salt) in er>99:1 enantiomeric purity (determined by chiral HPLC). For the subsequent reactions (R)-DNP-methylamine can be used as L-tosyl proline salt or as free base. In order to obtain the free base of (R)-DHP-methylamine, the L-tosyl proline salt is removed by treatment with a strong base, such as NaOH, preferably 2 N NaOH, according to the following scheme:

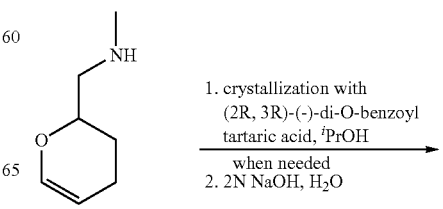

It is found for mixtures of compounds of formula C' wherein $R^1$ when $R^1$ is H and its antipode that the treatment with (2R,3R)-(−)-di-O-benzoyl tartaric acid in 2-propanol leads to crystals with the (R)-configured DHP-methylamine. The enantiomeric purity was determined by chiral HPLC to be er=84:16 for the desired (R)-DHP-methyl-N-methylamine enantiomer. Repeated recrystallization from 2-propanol provided the (R)-DHP-methyl-N-methylamine (as (2R,3R)-(−)-di-O-benzoyl tartaric acid in er>99:1 enantiomeric purity (determined by chiral HPLC). For the next reactions amine can be used as (2R,3R)-(−)-di-O-benzoyl tartaric acid salt or as free base. In order to get the free base the (2R,3R)-(−)-di-O-benzoyl tartaric acid salt of amine is removed by treatment with a strong base, such as NaOH, preferably 2N NaOH, according to the following scheme:

-continued

Free base or salt

In a preferred embodiment, enantiomerically pure DHP-methylamines can be transformed in different other compounds classes like substituted DHP-methylamines DHP-methylamides, DHP-methylureas, DHP-methylsulfonamides or tertiary DHP-methylamines from DHP-methylamine chiral salts or the corresponding free base according to the following scheme:

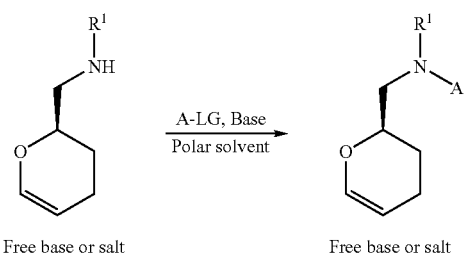

Free base or salt      Free base or salt wherein $R^1$ is as defined above and LG is a leaving group such as halogen, mesylate or tosylate, the base is a strong non nucleophilic base such as DBU or alkali-carbonate like such as $Na_2CO_3$ or $K_2CO_3$ and the solvent is a polar solvent such as DMF.

In a preferred embodiment, DNP-methylamides can be prepared by reacting acid $R^1$—COOH with DHP-methylamine chiral salts or the corresponding free base with a coupling agent and the presence or absence of a suitable base in a polar solvent according to the following scheme:

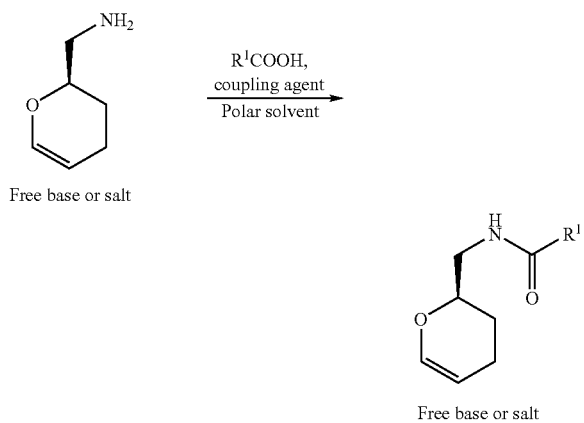

Free base or salt wherein $R^1$ is as defined above and the coupling agent is selected from BOP reagent, CDI, DCC, DEPBT, DIC, EDC.HCl, HATU, HBTU, HOAt, HOBt(anhydrous), HOOBt, HCTU, Cl—HOBt, PyBOP, PyBrOP, TBTU, TDBTU, TSTU or 4,5-dicyanoimidazole, the base, if needed, is selected from triethylamine or other alkylamines and the polar solvent is selected from DMF.

In a preferred embodiment, DHP-methylamides can be prepared by reacting acyl chloride $R^1$—COCl with DHP-methylamine chiral salts or the corresponding free base with the presence or absence of a suitable base in a polar solvent according to the following scheme:

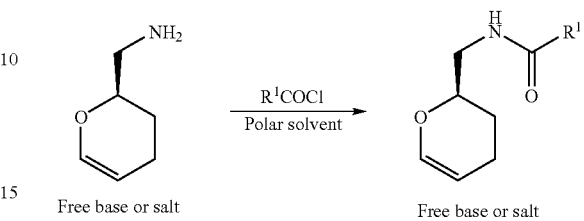

Free base or salt      Free base or salt wherein $R^1$ is as defined above and the base, if needed, is selected from triethylamine and other alkylamines and the polar solvent is selected from DMF.

In a preferred embodiment DHP-methylsulfonamides can be prepared by reacting sulfonyl chloride $R^1$—$SO_2Cl$ with DHP-methylamine chiral salts or the corresponding free base with the presence or absence of a suitable base in a polar solvent according to the following scheme:

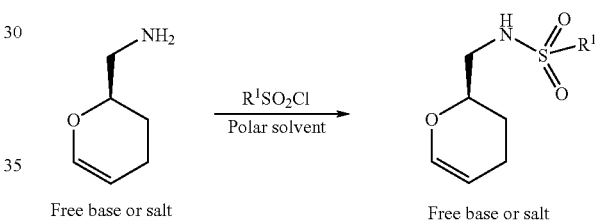

Free base or salt      Free base or salt wherein $R^1$ is as defined above and the base, if needed, is selected from triethylamine and other alkylamines and the polar solvent is selected from DMF.

In a preferred embodiment DHP-methylureas can be prepared by reacting the coupling agent CDI with DHP-methylamine chiral salts or the corresponding free base and primary amine $NH_2$—$R^1$ with the presence or absence of a suitable base in a polar solvent.

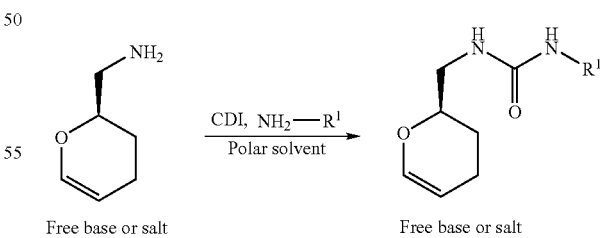

Free base or salt      Free base or salt

In a preferred embodiment, the invention relates to a process for the synthesis of compounds according to formula I wherein C derivatives such as DHP-amides, DHP-ureas, DHP-sulfonamides, and tertiary DHP-amines react in a multicomponent reaction mediated by a protonic acid or lewis acid in a polar solvent with anilines of type A and aldehydes of type B to form THQ derivatives.

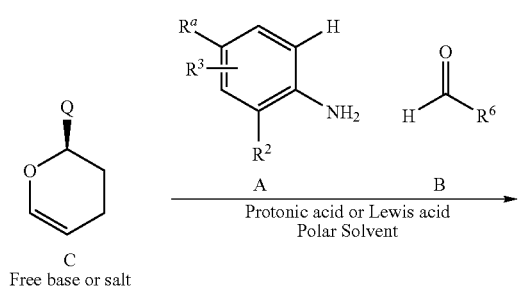

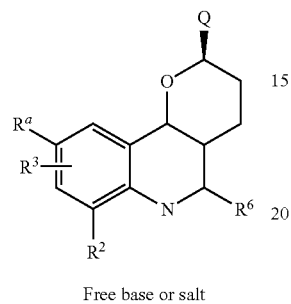

wherein $R^a$, $R^2$, $R^3$, $R^6$, Q are as defined above and the protonic acid is preferably TFA and the polar solvent is preferably MeCN.

In a more preferred embodiment, the invention relates to a process for the synthesis of compounds according to formula I wherein C' derivatives such as DHP-metylamides, DHP-methylureas, DHP-methylsulfonamides, or tertiary DHP-methylamines react in a multicomponent reaction mediated by a protonic acid or lewis acid in a polar solvent with anilines of type A and aldehydes of type B to form THQ derivatives.

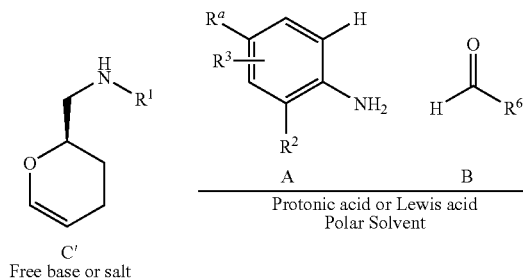

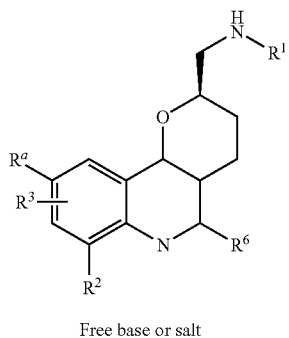

wherein $R^a$, $R^1$, $R^2$, $R^3$, $R^6$, are as defined above and the protonic acid is preferably TFA and the polar solvent is preferably MeCN.

In a more preferred embodiment the invention relates to a process for the synthesis of compounds according to formula I wherein C' derivatives such as DHP-methylamides, DHP-methylureas, DHP-methylsulfonamides, and tertiary DHP-methylamines react in a multicomponent reaction mediated by a protonic acid or lewis acid in a polar solvent with anilines of type A and Arylaldehydes of type B wherein $R^6$ is aryl, to form THQ.

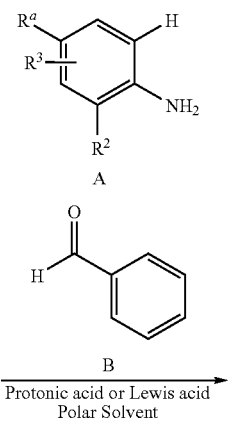

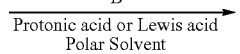

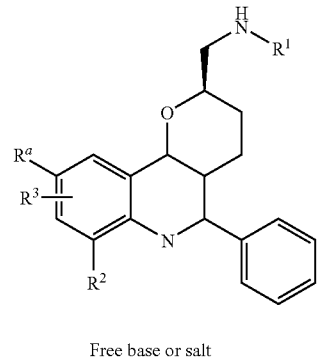

wherein $R^a$, $R^1$, $R^2$, $R^3$ are as defined above and the protonic acid is preferably TFA and the polar solvent is preferably MeCN.

In a more preferred embodiment the invention relates to a process for the synthesis of compounds according to formula I in a pure enantiomeric form wherein the THQ obtained previously from C is crystallized with chiral salts to give the corresponding exo-enantiomer of THQ.

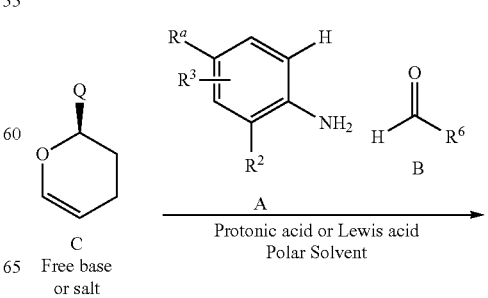

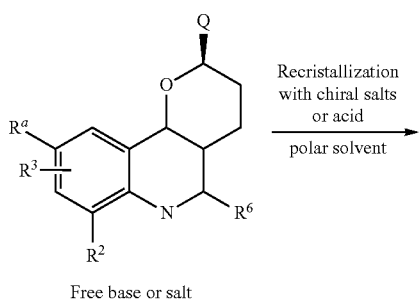

Free base or salt

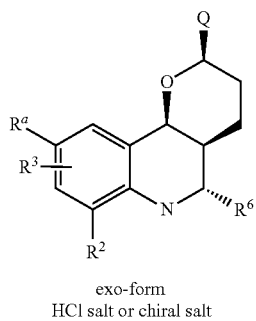

exo-form
HCl salt or chiral salt wherein $R^a$, $R^1$, $R^2$, $R^3$, $R^6$ are as defined above and the protonic acid is preferably TFA and the polar solvent is preferably MeCN. For the recrystallization step the chiral salts is selected from tartaric salts especially (2R,3R)-(−)-di-O-benzoyl tartaric acid and the polar solvent is ethanol.

In a more preferred embodiment the invention relates to a process for the synthesis of compounds according to formula I in a pure enantiomeric form wherein the THQ obtained previously from C' is crystallized with chiral salts to give the corresponding exo-enantiomer of THQ.

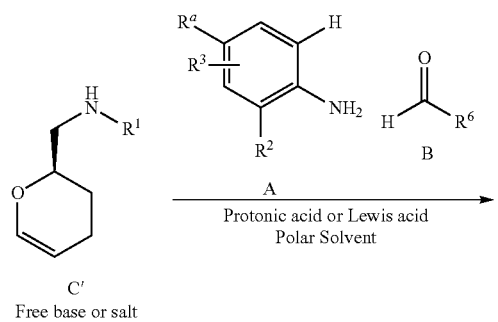

C'
Free base or salt

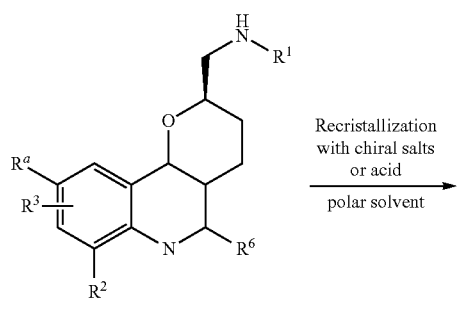

Free base or salt

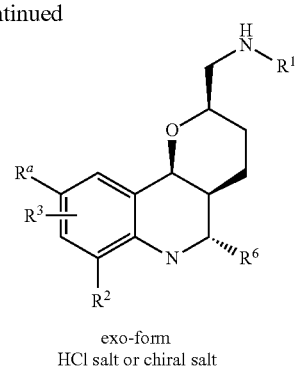

exo-form
HCl salt or chiral salt wherein $R^a$, $R^1$, $R^2$, $R^3$, $R^6$ are as defined above and the protonic acid is TFA and the polar solvent is MeCN. For the recrystallization step the chiral salts is selected from tartaric salts especially (2R,3R)-(−)-di-O-benzoyl tartaric acid and the polar solvent is ethanol.

In a more preferred embodiment the invention relates to a process for the synthesis of compounds according to formula I in a pure enantiomeric form wherein the THQ obtained previously from C is crystallized with chiral salts to give the corresponding exo-enantiomer of THQ.

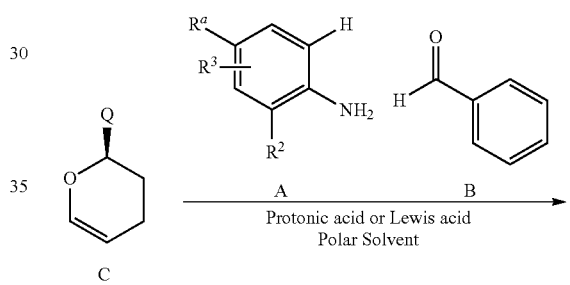

C
Free base or salt

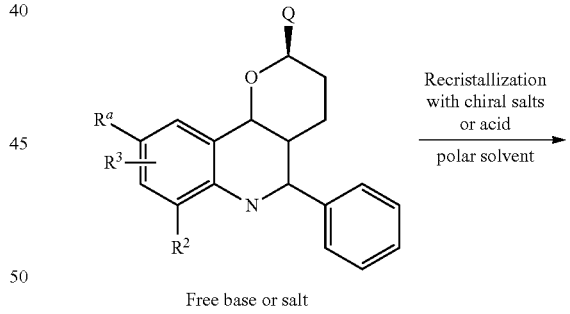

Free base or salt

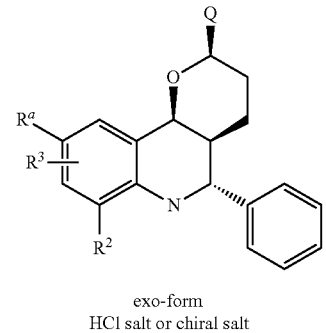

exo-form
HCl salt or chiral salt wherein $R^a$, $R^1$, $R^2$, $R^3$, are as defined above and the protonic acid is preferably TFA and the polar solvent is preferably MeCN. For the recrystallization step the chiral salts is selected from tartaric salts especially (2R,3R)-(−)-di-O-benzoyl tartaric acid and the polar solvent is preferably ethanol.

In a more preferred embodiment the invention relates to a process for the synthesis of compounds according to formula I in a pure enantiomeric form wherein the THQ obtained previously from C' is crystallized with chiral salts to give the corresponding exo-enantiomer of THQ.

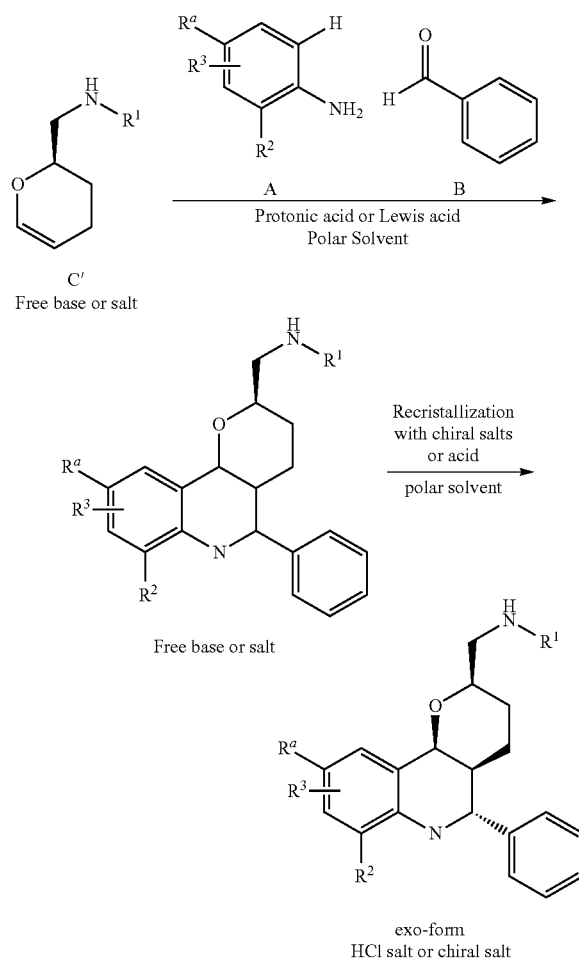

wherein $R^a$, $R^1$, $R^2$, $R^3$, are as defined above and preferably wherein $R^a$ is Cl, $R^1$ is $CH_3$, $R^2$ is F and $R^3$ is H, the protonic acid is preferably TFA and the polar solvent is preferably MeCN. For the recrystallization step the chiral salts is selected from tartaric salts especially (2R,3R)-(−)-di-O-benzoyl tartaric acid and the polar solvent is preferably ethanol.

EXAMPLES

A) Preparation of a Racemic C-(3,4-Dihydro-2H-pyran-2-yl)-methylamine

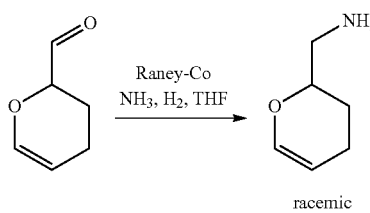

3,4-Dihydro-2H-pyran-2-carbaldehyde (950 g, 8.31 mol) was dissolved in precooled tetrahydrofuran (1.9 kg). Raney-Co catalyst (95 g, tetrahydrofuran moist) was added. Liquid ammonia (1350 g, 79.4 mol) was transferred into the solution within 15 minutes. Hydrogen (186.2 L) was adjusted to pressure 105 bar and the solution was stirred for 2 h at 100° C. The reaction vessel was cooled to room temperature, the gas removed and the solution degassed. The solution was concentrated under reduced pressure. The crude product (932 g) was distilled at reduced pressure to receive C-(3,4-Dihydro-2H-pyran-2-yl)-methylamine (702 g, 6.17 mmol, 74% yield). Analytical data: Bp. 77-82° C. (30-32 mbar); HPLC-MS: (M+H)+=114 at rt=0.665 min. (TIC), rt=0.644 min. (UV), rt=0.616 min. (ELS), Chromolith SpeedROD RP-18e 50-4.6 mm, solvent A: water+0.1% TFA, solvent B: acetonitrile+0.1% TFA, gradient: 4% solvent B at 0.0 min., 100% solvent B at 2.6 min., flow: 2.4 mL/min., UV: 220 nm.

B) Preparation of Racemic (3,4-Dihydro-2H-pyran-2-ylmethyl)-methyl-amine

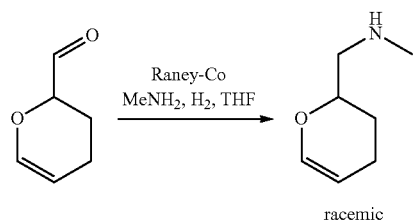

3,4-Dihydro-2H-pyran-2-carbaldehyde (300 g, 2.68 mol) was dissolved in tetrahydrofuran (710 mL). Raney-Co catalyst (30 g, tetrahydrofuran moist) was added. Gaseous methyl amine (415.4 g, 13.4 mol) was transferred into the solution within 50 minutes (45° C.). Hydrogen (49.2 L) was added and the pressure adjusted to 100 bar and the solution was stirred for about 2 h at 100° C. The reaction vessel was cooled to room temperature, the gas removed and the solution degassed. The solution was concentrated under reduced pressure. The crude product (344.5 g) was distilled at reduced pressure to receive (3,4-Dihydro-2H-pyran-2-ylmethyl)-methyl-amine (289.8 g, 2.28 mol, 85% yield). Analytical data amine (3,4-Dihydro-2H-pyran-2-ylmethyl)-methyl-amine: Bp. 55-57° C. at 16 mbar; HPLC-MS: (M+H)+=128 at $r_t$=0.619 min. (TIC), $r_t$=0.596 min. (UV), $r_t$=0.631 min. (ELS), Chromolith SpeedROD RP-18e 50-4.6 mm, solvent A: water+0.1% TFA, solvent B: acetonitrile+0.1% TFA, gradient: 4% solvent B at 0.0 min., 100% solvent B at 2.6 min., flow: 2.4 mL/min., UV: 220 nm.

C) Preparation of Enantiomerically Pure C-(3,4-Dihydro-2H-pyran-2-yl)-methylamine (L-tosylproline salt) and Enantiomerically Pure C-(3,4-Dihydro-2H-pyran-2-yl)-methylamine (Free Base)

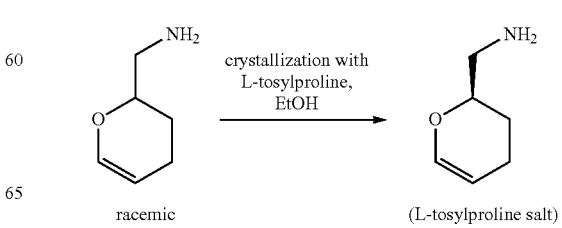

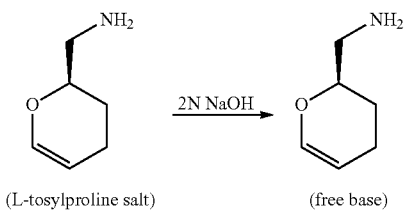

(L-tosylproline salt)    (free base)

Under gentle heating L-tosyl proline (119 g, 442 mmol) was dissolved in ethanol (1000 mL). The solution was filtrated and the filter rinsed out with hot ethanol (200 mL). C-(3,4-Dihydro-2H-pyran-2-yl)-methylamine (100 g, 884 mmol) and ethanol (200 mL) was added and heated to reflux. The solution was allowed to cool down under gentle stirring (~100 U/min.). At ~50° C. a small portion of seeding crystals of C-(3,4-Dihydro-2H-pyran-2-yl)-methylamine (er=>99.5: 0.5 by chiral HPLC, crystals derived from earlier experiments) were added. The solution was allowed to cool down to room temperature. During this time (18 h) a salt crystallized. The salt was filtered off and washed with a small amount of cold ethanol to yield amine salt C-(3,4-Dihydro-2H-pyran-2-yl)-methylamine (98.5 g, er=93.2:6.8 by chiral HPLC). In order to receive enantiopure crystals C-(3,4-Dihydro-2H-pyran-2-yl)-methylamine salt (98.5 g, er=93.2:6.8 by chiral HPLC) was dissolved under gentle heating in ethanol (850 mL) and crystallization was performed under the same conditions as described above to receive amine salt of C-(3,4-Dihydro-2H-pyran-2-yl)-methylamine (83.1 g, er=98.6:1.4 by chiral HPLC). C-(3,4-Dihydro-2H-pyran-2-yl)-methylamine salt (83.1 g, er=98.6:1.4 by chiral HPLC) was dissolved in ethanol (400 mL) and subjected to the same crystallization procedure as described above to yield C-(3,4-Dihydro-2H-pyran-2-yl)-methylamine salt (77.8 g, 46% of the theoretical yield, er=99.5:0.5 by chiral HPLC) in clear, colourless crystals. Analytical data C-(3,4-Dihydro-2H-pyran-2-yl)-methylamine salt: Mp. 177-178° C.; $[\alpha]_D^{20}$=−134.0° (c=0.995, MeOH); chiral HPLC: $r_tE1$=10.56 min., $r_tE2$=16.24 min. ($er_{E1/E2}$=0.5/99.5), Crownpak CR(+), $HClO_4$ pH1+10% methanol, flow: 0.8 mL/min., UV: 215 nm. C-(3,4-Dihydro-2H-pyran-2-yl)-methylamine salt (45.8 g, 120 mmol) was dissolved in water (100 mL) and 2 N aqueous NaOH (80 mL) was added. The solution was extracted five times with dichloromethane (100 mL). The organic layer was washed with water (50 mL) and dried with sodium sulphate to yield after distillation under reduced pressure C-(3,4-Dihydro-2H-pyran-2-yl)-methylamine (free base) (13.3 g, 98%, er=99.4:0.6 by chiral HPLC) as colourless liquid. Analytical data C-(3,4-Dihydro-2H-pyran-2-yl)-methylamine: Bp. 77-82° C. (30-32 mbar); $[\alpha]_D^{20}$=−75.8° (c=0.528, MeOH); chiral HPLC: $r_tE1$=10.2 min., $r_tE2$=14.7 min. ($er_{E1/E2}$=0.6/99.4), Crownpak CR(+), $HClO_4$ pH1+10% methanol, flow: 0.8 mL/min., UV: 215 nm.

D) Preparation of Enantiomerically Pure (3,4-Dihydro-2H-pyran-2-ylmethyl)-methyl-amine[(2R,3R)-(−)-Di-O-benzoyl Tartaric Acid Salt] and Free Base

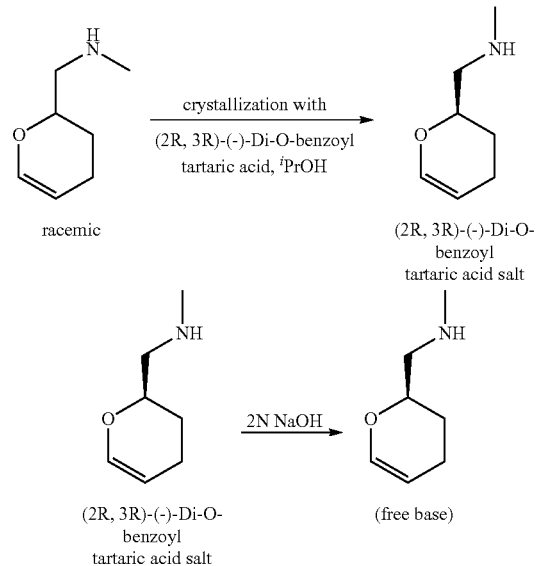

Under gentle heating (2R,3R)-(−)-di-O-benzoyl tartaric acid (47.0 g, 131 mmol) was dissolved in 2-propanol (400 mL). (3,4-Dihydro-2H-pyran-2-ylmethyl)-methyl-amine (50.0 g, 393 mmol, dissolved in 50 mL 2-propanol) was added and heated to reflux (~70° C., ~5 min.). The solution was allowed to cool down under gentle stirring (~100 U/min.). At ~50° C. a small portion of seeding crystals of (3,4-Dihydro-2H-pyran-2-ylmethyl)-methyl-amine (er=>99.5:0.5 by chiral HPLC, crystals derived from earlier experiments) were added. The solution was allowed to cool down to room temperature. During this time (18 h) a salt crystallized. The salt was filtered off and washed with a small amount of cold 2-propanol and n-heptane to yield (3,4-Dihydro-2H-pyran-2-ylmethyl)-methyl-amine salt (36.0 g, er=83.7:16.3 by chiral HPLC). In order to receive enantiopure crystals (3,4-Dihydro-2H-pyran-2-ylmethyl)-methyl-amine salt (36.0 g, er=83.7:16.3 by chiral HPLC) was dissolved under gentle heating in 2-propanol (360 mL) and crystallization was performed under the same conditions as described above to receive (3,4-Dihydro-2H-pyran-2-ylmethyl)-methyl-amine salt (25.7 g, er=95.5:4.5 by chiral HPLC). (3,4-Dihydro-2H-pyran-2-ylmethyl)-methyl-amine salt (25.7 g, er=95.5:4.5 by chiral HPLC) was dissolved in 2-propanol (350 mL) and subjected to the same crystallization procedure as described above to yield (3,4-Dihydro-2H-pyran-2-ylmethyl)-methyl-amine salt (20.6 g, 46% of the theoretical yield, er=99.5:0.5 by chiral HPLC) in clear, colourless crystals. Analytical data (3,4-Dihydro-2H-pyran-2-ylmethyl)-methyl-amine salt: Mp. 147-148° C.; $[\alpha]_D^{20}$=−111.1° (c=1.013, MeOH); chiral HPLC after derivatisation with (S)-(+)-MTPA-Cl: $r_tE1$=7.17 min., $r_tE2$=8.13 min. ($er_{E1/E2}$=0.5/99.5), Chiralcel OD-H, n-heptane/2-propanol 98:2, flow: 0.8 mL/min., UV: 240 nm; chiral GC-MS: RT-BetaDEXsm (length: 30 m, diameter: 0.25 mm), MS detector, gas: He (1.0 bar), column temperature: 50-150° C. (temperature program: 5° C./min.), injection temperature: 250° C.

(3,4-Dihydro-2H-pyran-2-ylmethyl)-methyl-amine salt (9.2 g, 15.0 mmol) was dissolved in water (25 mL) and 2 N aqueous NaOH (16 mL) was added. The solution was extracted five times with dichloromethane (100 mL). The organic layer was washed with water (50 mL) and dried with sodium sulphate to yield after distillation under reduced pressure (3,4-Dihydro-2H-pyran-2-ylmethyl)-methyl-amine (free base) (2.7 g, 72%, er=99.5:0.5 by chiral HPLC) as colourless liquid. Analytical data (3,4-Dihydro-2H-pyran-2-ylmethyl-methyl-amine (free base): Bp. 55-57° C. at 16 mbar. $[\alpha]_D^{20}$=−86.2° (c=0.725, MeOH); HPLC-MS: (M+H)$^{30}$=128 at $r_t$=0.619 min. (TIC), $r_t$=0.596 min. (UV), $r_t$=0.631 min. (ELS), Chromolith SpeedROD RP-18e 50-4.6 mm, solvent A: water+0.1% TFA, solvent B: acetonitrile+0.1% TFA, gradient: 4% solvent B at 0.0 min., 100% solvent B at 2.6 min., flow: 2.4 mL/min., UV: 220 nm; chiral HPLC after derivatisation with (S)-(+)-MTPA-Cl: $r_t$E1=7.31 min., $r_t$E2=8.24 min. (er$_{E1/E2}$=0.5/99.5), Chiralcel OD-H, n-heptane/2-propanol 98:2, flow: 0.8 mL/min., UV: 240 nm.

E) Preparation of Enantiomerically Pure 1-[(R)-1-(3,4-Dihydro-2H-pyran-2-yl)methyl]-3-(2-dimethylamino-ethyl)-urea

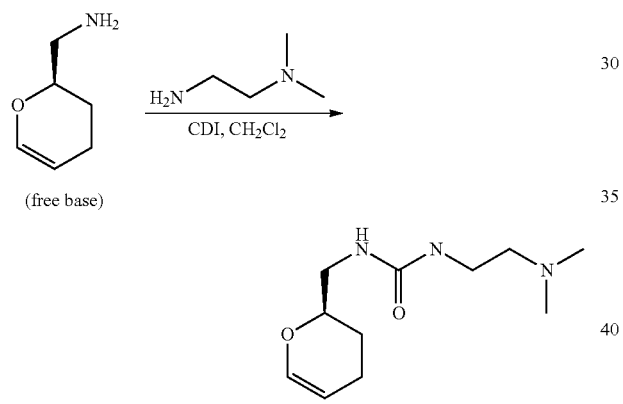

C-(3,4-Dihydro-2H-pyran-2-yl)-methylamine (free base) (13.3 g, 118 mmol) and 1,1'-carbonyl diimidazole (28.6 g, 176 mmol) were dissolved in dichloromethane (900 mL) and stirred for 2 h at room temperature. Under an Argon atmosphere N,N-Dimethyl ethylene diamine [51.2 mL, 470 mmol; dissolved in dichloromethane (250 mL)] was added and the reaction mixture stirred for 65 h at room temperature. The reaction mixture was concentrated to about one third volume under reduced pressure and extracted three times with water (100 mL). The organic layer was dried with sodium sulphate and the remaining solvent removed under reduced pressure to yield 1-[(R)-1-(3,4-Dihydro-2H-pyran-2-yl)methyl]-3-(2-dimethylamino-ethyl)urea (24.2 g, 91%) as pale yellow liquid. Analytical data 1-[(R)-1-(3,4-Dihydro-2H-pyran-2-yl)methyl]-3-(2-dimethylamino-ethyl)-urea: HPLC-MS: (M+H)$^+$=228.2 at $r_t$=1.155 min., column: Chromolith SpeedROD RP-18e 50-4, 6 mm; solvent A: water+0.1% TFA, solvent B: acetonitrile+0.1% TFA, gradient: 4% B at 0.0 min, 100% B at 2.6 min., 100% B at 3.3 min, flow: 2.4 mL/min., UV: 220 nm.

F1) Preparation of Diastereomerically and Enantiomerically Pure exo-1-(2-Dimethylamino-ethyl)-3-(2R,4aS,5R,10bS)-5-phenyl-9-trifluoromethyl-3,4,4a,5,6,10b-hexahydro-2H-pyrano[3,2-c]quinolin-2-ylmethyl)-urea

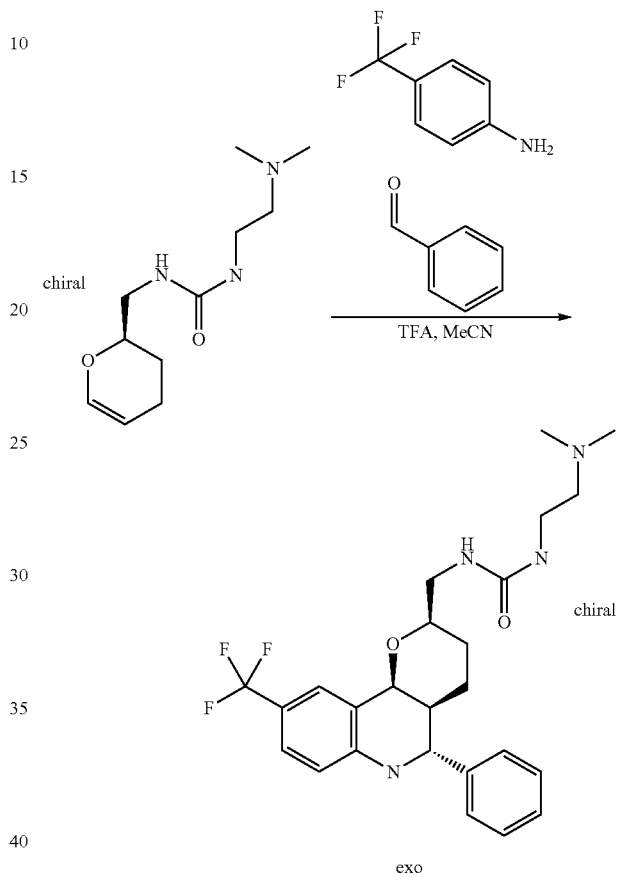

1-[(R)-1-(3,4-Dihydro-2H-pyran-2-yl)methyl]-3-(2-dimethylamino-ethyl)-urea (24.2 g, 106 mmol) and benzaldehyde (11.0 mL, 108 mmol) were dissolved in acetonitrile (100 mL) at ~5° C. (ice-bath). A precooled (~5° C.) solution of 4-aminobenzotrifluoride (17.55 g, 109 mmol) and TFA (16.1 mL) in acetonitrile (100 mL) was added and the reaction mixture stirred for additional 2 h at ~5° C. The reaction temperature was allowed to rise to room temperature and stirred additional 90 h. The solvents were removed under reduced pressure, the residue dissolved in ethyl acetate and extracted three times with water (100 mL). The organic layer was dried with sodium sulphate and the solvents removed under reduced pressure. The resulting crude diastereomeric mixture exo- and endo-1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea (48.6 g) was dissolved in dichloromethane (1.4 L) and extracted with water (300 mL), with saturated aqueous sodium bicarbonate (300 mL), and again with water (300 mL). The organic layer was dried with sodium sulphate and the solvents removed under reduced pressure to receive the THQ-urea as diastereomeric mixture exo- and endo-1-(2-Dimethylamino-ethyl)-3-((2R,4aS,5R,10bS)-5-phenyl-9-trifluoromethyl-3,4,4a,5,6,10b-hexahydro-2H-pyrano[3,2-c]

quinolin-2-ylmethyl)-urea (34.5 g). Analytical data mixture exo- and endo-1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea: HPLC-MS: endo-1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea with (M+H)$^+$=477 at $r_t$=1.932 min. (TIC), $r_t$=1.903 min. (UV), $r_t$=1.901 min. (ELS) and exo-1-(2-Dimethylamino-ethyl)-3-(2R,4aS,5R,10bS)-5-phenyl-9-trifluoromethyl-3,4,4a,5,6,10b-hexahydro-2H-pyrano[3,2-c]quinolin-2-ylmethyl)-urea with (M+H)$^+$=477 at $r_t$=2.062 min. (TIC), $r_t$=2.035 min. (UV), $r_t$=2.033 min. (ELS), Chromolith SpeedROD RP-18e 50-4.6 mm, solvent A: water+0.1% TFA, solvent B: acetonitrile+0.1% TFA, gradient: 4% solvent B at 0.0 min., 100% solvent B at 2.6 min., flow: 2.4 ml/min., UV: 220 nm.

The residue was subjected to column chromatography (Si60, 0.063-0.2 mm; dichloromethane/methanol 95:5 to 70:30). The suitable fractions were collected and the solvents removed under reduced pressure to receive pure THQ diastereomer exo-1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea (19.1 g, 38%). Analytical data exo-1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea: Mp. 121° C.; $[\alpha]_D^{20}$=−75.7° (c=1.02, EtOH); HPLC: $r_t$exo=10.6 min., $r_t$endo=12.7 min., Purospher Star, solvent: $^n$heptane/EtOH 80:20+0.5% diethyl amine, flow: 1 mL/min., UV: 250 nm; HPLC-MS: (M+H)$^+$=477 at $r_t$=2.062 min. (TIC), $r_t$=2.035 min. (UV), $r_t$=2.033 min. (ELS), Chromolith SpeedROD RP-18e 50-4.6 mm, solvent A: water+0.1% TFA, solvent B: acetonitrile 0.1% TFA, gradient: 4% solvent B at 0.0 min., 100% solvent B at 2.6 min., flow: 2.4 mL/min., UV: 220 nm.

F2) Separation of THQ Diastereomers Exo- and Endo-1-(2-Dimethylamino-ethyl)-3-(2R,4aS,5R,10bS)-5-phenyl-9-trifluoromethyl-3,4,4a,5,6,10b-hexahydro-2H-pyrano[3,2-c]quinolin-2-ylmethyl)-urea via preparative HPLC

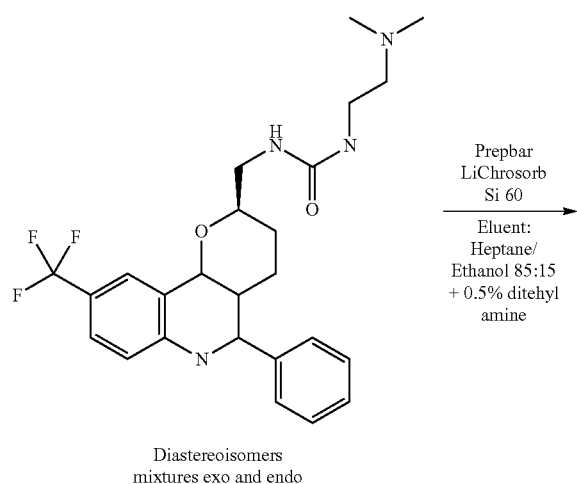

Diastereoisomers mixtures exo and endo

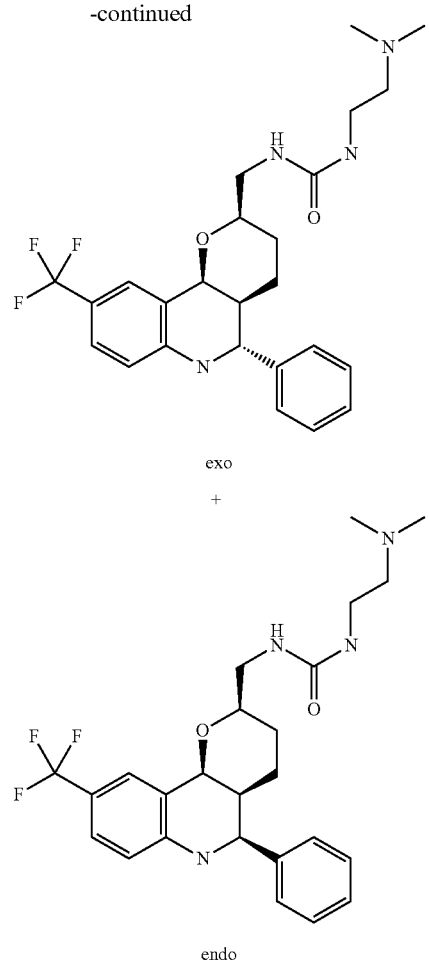

exo
+ endo

The pure diastereomers of a diastereomeric mixture of urea exo- and endo-1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea (5.7 g) were separated via preparative HPLC (column: Prepbar LiChrosorb Si60 10 μm, 25×5 cm; eluent: $^n$heptane/ethanol 85:15+0.5% diethyl amine, injection: 250 mg/10 mL, flow: 80 mL/min., UV: 254 nm) to receive THQ-urea exo-1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea (2.1 g, 4.4 mmol) and THQ-urea endo-1-(2-Dimethylamino-ethyl)-3-(2R,4aS,5R,10bS)-5-phenyl-9-trifluoromethyl-3,4,4a,5,6,10b-hexahydro-2H-pyrano[3,2-c]quinolin-2-ylmethyl)-urea (1.8 g, 3.8 mmol) as pure diastereomers. Analytical data exo-1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea: see section F1 Analytical data endo-1-(2-Dimethylamino-ethyl)-3-(2R,4aS,5R,10bS)-5-phenyl-9-trifluoromethyl-3,4,4a,5,6,10b-hexahydro-2H-pyrano[3,2-c]quinolin-2-ylmethyl)-urea: HPLC-MS: (M+H)$^+$=477 at $r_t$=1.932 min. (TIC), $r_t$=1.903 min. (UV), $r_t$=1.901 min. (ELS), Chromolith SpeedROD RP-18e 50-4.6 mm, solvent A: water+0.1% TFA, solvent B: acetonitrile+0.1% TFA, gradient: 4% solvent B at 0.0 min., 100% solvent B at 2.6 min., flow: 2.4 mL/min., UV: 220 nm.

G) Preparation of Diastereomerically and Enantiomercally Pure C ((2R,4aS,5R,10bS)-5-Phenyl-9-trifluoromethyl-3,4,4a,5,6,10b-hexahydro-2H-pyrano[3,2-c]quinolin-2-yl)-methylamine

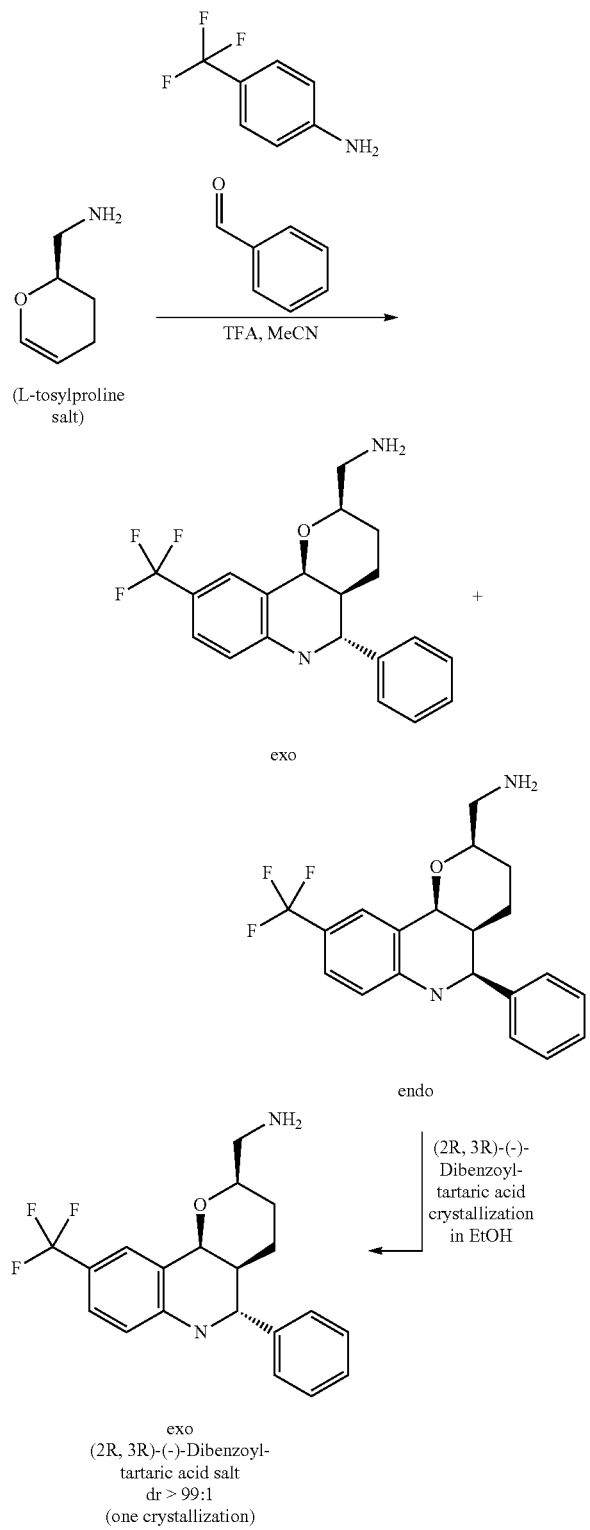

C-[(R)-1-(3,4-Dihydro-2H-pyran-2-yl)]methylamine salt (77 g, 201 mmol) and benzaldehyde (20.7 mL, 205 mmol) were dissolved in acetonitrile (185 mL) at ~5° C. (ice-bath). A precooled (~5° C.) solution of 4-aminobenzotrifluoride (33.0 g, 205 mmol) and TFA (31.7 mL) in acetonitrile (185 mL) was added fast and the reaction mixture stirred for additional 2 h at ~5° C. The reaction temperature was allowed to rise to room temperature and stirred additional 35 h. The solvents were removed under reduced pressure, the residue treated with water and saturated aqueous sodium bicarbonate solution until pH 8-9 was reached. Ethyl acetate (300 mL) was added and the organic layer was extracted one time with saturated aqueous sodium bicarbonate solution (200 mL) and three times with water (150 mL). The organic layer was dried with sodium sulphate and the solvents were removed under reduced pressure to yield a crude diastereomeric mixture exo- and endo-C ((2R,4aS,5R,10bS)-5-Phenyl-9-trifluoromethyl-3,4,4a,5,6,10b-hexahydro-2H-pyrano[3,2-c]quinolin-2-yl)-methylamine (98.4 g, dr ~1:1 [exo/endo]). Analytical data mixture exo- and endo-C ((2R,4aS,5R,10bS)-5-Phenyl-9-trifluoromethyl-3,4,4a,5,6,10b-hexahydro-2H-pyrano[3,2-c]quinolin-2-yl)-methylamine: HPLC-MS: endo-C ((2R,4aS,5R,10bS)-5-Phenyl-9-trifluoromethyl-3,4,4a,5,6,10b-hexahydro-2H-pyrano[3,2-c]quinolin-2-yl)-methylamine with $(M+H)^+=363$ at $r_t=1.913$ min. (TIC), $r_t=1.883$ min. (UV), $r_t=1.879$ min, (ELS) and endo-C ((2R,4aS,5R,10bS)-5-Phenyl-9-trifluoromethyl-3,4,4a,5,6,10b-hexahydro-2H-pyrano[3,2-c]quinolin-2-yl)-methylamine with $(M+H)^+=363$ at $r_t=2.021$ min. (TIC), $r_t=1.990$ min. (UV), $r_t=1.988$ min. (ELS), Chromolith SpeedROD RP-18e 50-4.6 mm, solvent A: water+0.1% TFA, solvent B: acetonitrile 0.1% TFA, gradient: 4% solvent B at 0.0 min., 100% solvent B at 2.6 min., flow: 2.4 mL/min., UV: 220 nm.

The crude diastereomeric mixture exo- and endo-C ((2R,4aS,5R,10bS)-5-Phenyl-9-trifluoromethyl-3,4,4a,5,6,10b-hexahydro-2H-pyrano[3,2-c]quinolin-2-yl)-methylamine (80.5 g), was dissolved in 2-propanol (400 mL) under gentle heating and (2R,3R)-(–)-di-O-benzoyl tartaric acid was added. The reaction mixture was further heated to reflux until a clear solution was formed. The solution was allowed to cool down to room temperature over the next 20 h. For additional 4 h the reaction mixture was cooled down to 0° C. (ice-bath). During this time a salt crystallized. The salt was filtered off and washed with a small amount of cold 2-propanol to give single diastereomeric THQ-amine salt exo-C ((2R,4aS,5R,10bS)-5-Phenyl-9-trifluoromethyl-3,4,4a,5,6,10b-hexahydro-2H-pyrano[3,2-c]quinolin-2-yl)-methylamine (14.7 g, 24%, er=99.9:0.1 by chiral HPLC). Analytical data exo-C ((2R,4aS,5R,10bS)-5-Phenyl-9-trifluoromethyl-3,4,4a,5,6,10b-hexahydro-2H-pyrano[3,2-c]quinolin-2-yl)-methylamine: Mp. 169-171° C.; $[\alpha]_D^{20}=-105.1°$ (c=1.11, MeOH); chiral HPLC: $r_t$endo=12.75 min., $r_t$exo=14.93 min. ($dr_{endo/exo}=02199.8$), Chirobiotic T2, methanol+0.04% ammonium trifluoro acetate (AFTA), flow: 1.0 mL/min., UV: 265 nm.

H) Preparation of Diastereomerically and Enantiomerically Pure THQ-amine exo-((2R,4aS,5R,10bS)-9-Chloro-7-fluoro-5-phenyl-3,4,4a,5,6,10b-hexahydro-2H-pyrano[3,2-c]quinolin-2-ylmethyl)-methyl-amine

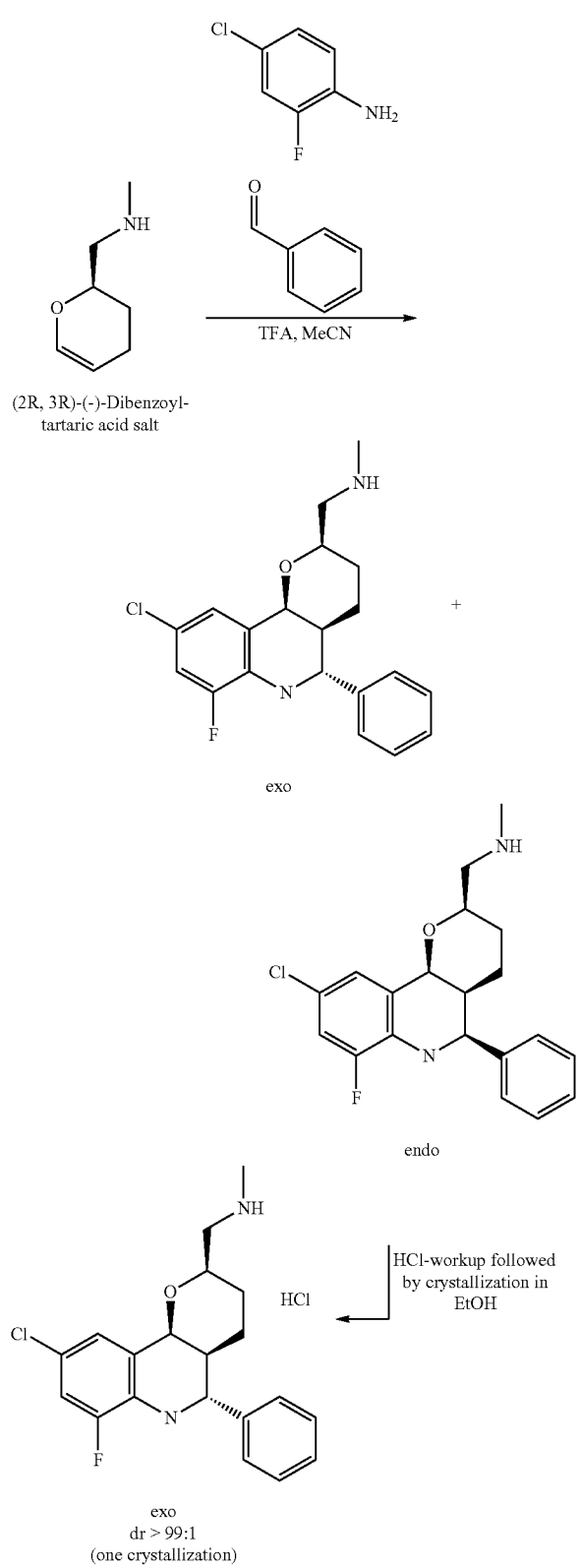

Aniline derivative (19.7 g, 135.5 mmol) and benzaldehyde (14.4 g, 135.8 mmol) were dissolved in acetonitrile (250 mL) and stirred for 3 h at 60-70° C. The solution was cooled down (ice-bath). (3,4-Dihydro-2H-pyran-2-ylmethyl)-methyl-amine [(2R,3R)-(−)-Di-O-benzoyl tartaric acid salt] (40.0 g, 65.3 mmol) and immediately afterwards TFA (50 mL, dissolved in 100 mL acetonitrile) was added and the reaction mixture stirred for additional 1 h in an ice-bath an additional 18 h at room temperature. The solvent and most of the TFA were removed under reduced pressure, the residue dissolved in dichloromethane (500 mL) and extracted with 2 N NaOH (350 mL). The organic layer was further diluted with dichloromethane (300 mL) and extracted twice with water (200 mL portions). The organic layer was extracted four times with 2 N HCl (200 mL portions) and twice with water (200 mL portions). Both layers were collected. From the aqueous layer a red-brown oil excreted overnight that was dissolved in dichloromethane (100 mL) and the mixture was conflated with the organic layer. The combined organic layer was dried with sodium sulphate and the solvents were removed under reduced pressure to yield a crude diastereomeric mixture exo- and endo-((2R,4aS,5R,10bS)-9-Chloro-7-fluoro-5-phenyl-3,4,4a,5,6,10b-hexahydro-2H-pyrano[3,2-c]quinolin-2-ylmethyl)-methyl-amine (21.05 g). Analytical data mixture exo- and endo-((2R,4aS,5R,10bS)-9-Chloro-7-fluoro-5-phenyl-3,4,4a,5,6,10b-hexahydro-2H-pyrano[3,2-c]quinolin-2-ylmethyl)-methyl-amine HPLC-MS: endo-((2R,4aS,5R,10bS)-9-Chloro-7-fluoro-5-phenyl-3,4,4a,5,6,10b-hexahydro-2H-pyrano[3,2-c]quinolin-2-ylmethyl)-methyl-amine with $(M+H)^+=361$ at $r_t=1.928$ min. (TIC), $r_t=1.902$ min. (UV), $r_t=1.863$ min (ELS) and exo-((2R,4aS,5R,10bS)-9-Chloro-7-fluoro-5-phenyl-3,4,4a,5,6,10b-hexahydro-2H-pyrano[3,2-c]quinolin-2-ylmethyl)-methyl-amine with $(M+H)^+=361$ at $r_t=2.043$ min. (TIC), $r_t=2.013$ min. (UV), $r_t=1.976$ min. (ELS), Chromolith SpeedROD RP-18e 50-4.6 mm, solvent A: water+0.1% TFA, solvent B: acetonitrile+0.1% TFA, gradient: 4% solvent B at 0.0 min., 100% solvent B at 2.6 min., flow: 2.4 mL/min., UV: 220 nm.

The crude diastereomeric mixture exo- and endo-((2R,4aS,5R,10bS)-9-Chloro-7-fluoro-5-phenyl-3,4,4a,5,6,10b-hexahydro-2H-pyrano[3,2-c]quinolin-2-ylmethyl)-methyl-amine (21.05 g), was dissolved in ethanol (160 mL) under gentle heating and the reaction mixture was allowed to cool to room temperature under gentle steering over 18 hours. Finally the reaction mixture was stirred for additional 3 h in an ice-bath. The resulting crystals were collected by filtration and washed with a small amount of cold 2-propanole and n-heptane to yield THQ-amine salt exo-(2R,4aS,5R,10bS)-9-Chloro-7-fluoro-5-phenyl-3,4,4a,5,6,10b-hexahydro-2H-pyrano[3,2-c]quinolin-2-ylmethyl)-methyl-amine (4.34 g, 16.7%, dr=99.5:0.5 and er>99.8:0.2 by chiral HPLC) as colourless crystals. Analytical data exo-((2R,4aS,5R,10bS)-9-Chloro-7-fluoro-5-phenyl-3,4,4a,5,6,10b-hexahydro-2H-pyrano[3,2-c]quinolin-2-ylmethyl)-methyl-amine: Mp. 295-296° C.; $[\alpha]_D^{20}=-22.8°$ (c=1.93, MeOH); chiral HPLC: $r_t$E1exo=14.3 min., Chiralpak AD, n-heptane/2-propanol 95:5+0.5% diethyl amine, flow: 0.8 mL/min., UV: 254 nm.

The remaining reaction mixture was concentrated under reduced pressure. The residue was dissolved in 2-propanol (150 mL) under gentle heating. Seeding crystals of the first crystallization were added after the reaction mixture cooled to room temperature and the reaction mixture stirred for additional 64 h. Afterwards the reaction mixture was cooled in an ice-bath for 4 h. The resulting crystals were collected by filtration and washed with a little amount of cold 2-propanol and n-heptane respectively to give further THQ-amine salt exo-((2R,4aS,5R,10bS)-9-Chloro-7-fluoro-5-phenyl-3,4,4a, 5,6,10b-hexahydro-2H-pyrano[3,2-c]quinolin-2-ylmethyl)-methyl-amine (1.41 g, dr=90.3:9.7 and er>99.8:0.2 by chiral HPLC) as colourless crystals.

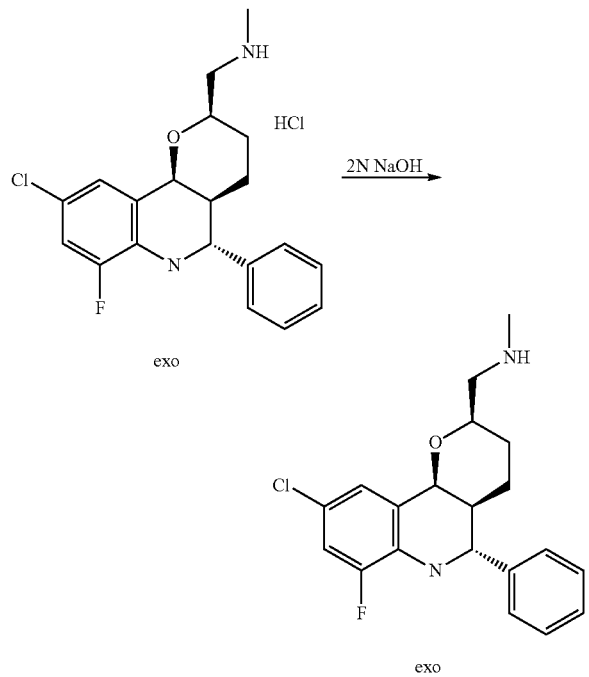

exo

THQ-amine salt exo-((2R,4aS,5R,10bS)-9-Chloro-7-fluoro-5-phenyl-3,4,4a,5,6,10b-hexahydro-2H-pyrano[3,2-c]quinolin-2-ylmethyl)-methyl-amine (0.95 g, 2.39 mmol) was dissolved in 2 N aqueous NaOH (10 mL). Dichloromethane (30 mL) was added and the reaction mixture vigorously shaken until all the solids were completely dissolved. The layers were separated and the aqueous layer was saturated with sodium chloride and extracted twice with dichloromethane (20 mL). The combined organic layers were washed with water (5 mL) and dried with sodium sulphate to yield amine (free base) exo-((2R,4aS,5R,10bS)-9-Chloro-7-fluoro-5-phenyl-3,4,4a,5,6,10b-hexahydro-2H-pyrano[3,2-c]quinolin-2-ylmethyl)-methyl-amine (0.84 g, 97%, dr>99.8: 0.2 and er>99.8:0.2 by chiral HPLC) as colourless crystals. Analytical data exo-((2R,4a8,5R,10bS)-9-Chloro-7-fluoro-5-phenyl-3,4,4a,5,6,10b-hexahydro-2H-pyrano[3,2-c]quinolin-2-ylmethyl)-methyl-amine: Mp. 190-192° C.; $[\alpha]_D^{20}=-32.9°$ (c=1.09, MeOH); chiral HPLC: $r_t$E1exo=15.8 min., Chiralpak AD, n-heptane/2-propanol 95:5+0.5% diethyl amine, flow: 0.8 mL/min., UV: 254 nm.

I) Alternative Preparation of Diastereomerically and Enantiomerically Pure THQ-urea exo-1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea

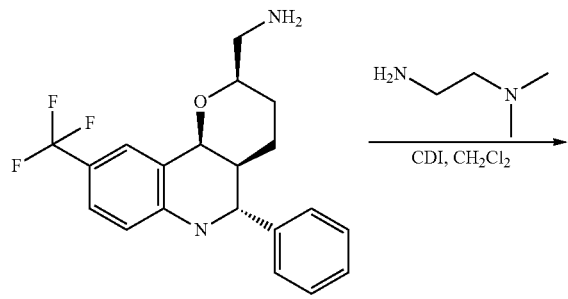

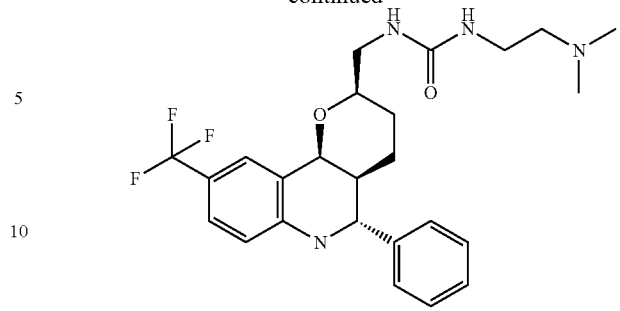

THQ amine (−)-dibenzoyl tartaric acid salt exo-C-((2R,4aS,5R,10bS)-5-Phenyl-9-trifluoromethyl-3,4,4a,5,6,10b-hexahydro-2H-pyrano[3,2-c]quinolin-2-yl)-methylamine (14.5 g, 13.4 mmol) and 1,1'-carbonyl diimidazole (6.5 g, 40.1 mmol) were dissolved in dichloromethane (300 mL) and stirred for 2 h at room temperature. Under an Argon atmosphere N,N-Dimethyl ethylene diamine [11.7 mL, 107 mmol; dissolved in dichloromethane (70 mL)] was added and the reaction mixture stirred for 18 h at room temperature. The solvents were removed under reduced pressure. The residue was dissolved in ethyl acetate and extracted two times with 1 N aqueous NaOH (80 mL) and three times with water (250 mL). The organic layer was dried with sodium sulphate and the remaining solvent removed under reduced pressure. The residue (approx. 15 g) was dissolved in dichloromethane (40 mL) and gentle warming. MTBE (80 mL) was added and the mixture cooled in an ice-bath for 18 h. The resulting crystals were collected by filtration and washed with an ice-cold solution of dichloromethane/MTBE 1:4 to receive THQ amine exo-13a (6.38 g, 99%) as colourless crystals. Analytical data exo-1-(2-Dimethylamino-ethyl)-3-((2R,4aS,5R,10bS)-5-phenyl-9-trifluoromethyl-3,4,4a,5,6,10b-hexahydro-2H-pyrano[3,2-c]quinolin-2-ylmethyl)-urea: see section F1 analytical data.

Abbreviations: MeOH=methanol; EtOH=ethanol, PrOH=propanol, $^i$PrOH=isopropanol, DMF=dimethylformamide, THF=tetrahydrofuran, THQ=tetrahydroquinoline; DHP=3,4-Dihydro-2H-pyran, TFA=trifluoroacetic acid; CDI=1,1'-carbonyldiimidazole; MeCN (Acetonitrile), BOP=Benzotriazole-1-yl-oxy-tris-(dimethylamino)-phosphonium hexafluorophosphate, DCC=Dicyclohexylcarbodiimide, DEPBT=3-(Diethoxyphosphoryloxy)-3H-benzo[d][1,2,3]triazin-4-one, DIC=N,N'-Diisopropylcarbodiimide, EDC=1-Ethyl-3-(3-dimethylaminopropyl)carbodiimide hydrochloride, HATU=2-(1H-7-Azabenzotriazol-1-yl)-1,1,3,3-tetramethyl uronium hexafluorophosphate Methanaminium, HBTU=O-Benzotriazole-N,N,N',N'-tetramethyl-uronium-hexafluoro-phosphate, HOAt=[1,2,3]Triazolo[4,5-b]pyridin-3-ol, HOBt=N-Hydroxybenzotriazole, HOOBt=Hydroxy-3,4-dihydro-4-oxo-1,2,3-benzotriazine, HCTU=1H-Benzotriazolium 1-[bis(dimethylamino)methylene]-5chloro-hexafluorophosphate (1-),3-oxide, Cl—HOBt=6-Chloro-1-Hydroxy-1H-Benzotriazole, PyBOP=Benzotriazol-1-yl-oxytripyrrolidinophosphonium hexafluorophosphate, PyBrOP=Bromo-tris-pyrrolidino phosphonium hexafluoro phosphate, TBTU=O-(Benzotriazol-1-yl)-N,N,N',N'-tetramethyluronium tetrafluoroborate, TDBTU=N,N,N',N'-Tetramethyl-O-(3,4-dihydro-4-oxo-1,2,3-benzotriazin-3-yl)uronium tetrafluoroborate, TSTU=O—(N-Succinimidyl)-1,1,3,3-tetramethyluronium tetrafluoroborate, 4,5-Dicyanoimidazole, MTBE=tert.-Butyl methyl ether; $r_t$=retention time; UV=ultraviolet dector; TIC=total ion count (MS detector);

ELS=evaporating light scattering (detector type); Mp.=melting point; Bp.=boiling point, er=enantiomeric ratio; dr=diastereomeric ratio.

Equipment: optical rotation—Perkin Elmer Polarimeter 341 (c is measured in g/100 mL, 100 mm cell); melting point—Büchi Melting Point B-545 (all melting points are uncorrected); chiral HPLC—Merck-Hitachi LaChrom (consisting of D-7000 interface, L-7100 pump, L-7200 auto sampler, L-7300 column oven, L-7400 diode array detector), HPLC-MS—Agilent 1100 System (MS & DAD) with ELS-detector Sedex 75 from ERC.

The invention claimed is:

1. A process for the manufacture of an enantiomerically enriched or pure compound of formula I:

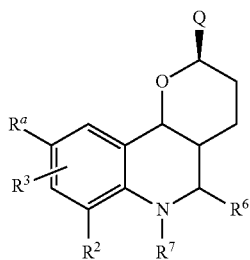

I wherein
$R^a$ denotes Hal, cyano, COOH, COOA, A, $CF_3$;
$R^1$ denotes H, A, Ar, Het, Hal, $—(CY_2)_n—SA$, $—(CY_2)_n—SCF_3$, $—(CY_2)_n—SCN$, $—(CY_2)_n—CF_3$, $—(CY_2)_n—OCF_3$, R, cycloalkyl, $—SCH_3$, $—SCN$, $—CF_3$, $—OCF_3$, $—OA$, $—(CY_2)_n—OH$, $—(CY_2)_n—CO_2R$, $—(CY_2)_n—CN$, $—(CY_2)_n$-Hal, $—(CY_2)_n—NR_2$, $(CY_2)_n—OA$, $(CY_2)_n—OCOA$, $—SCF_3$, $(CY_2)_n—CONR_2$, $—(CY_2)_n—NHCOA$, $—(CY_2)_n—NHSO_2A$, $SF_5$, $Si(CH_3)_3$, $CO—(CY_2)_n—CH_3$, $—(CY_2)_n—N$-Pyrrolidone, $(CH_2)_nNRCOOR$, NRCOOR, NCO, $(CH_2)_nCOOR$, NCOOR, $(CH_2)_nOH$, $NR(CH_2)_nNR_2$, $C(OH)R_2$, $NR(CH_2)_nOR$, NCOR, $(CH_2)_nAr$, $(CH_2)_nHet$, $(CH_2)_nR$, $(CH_2)_nX(CH_2)_nAr$, $(CH_2)_nX(CH_2)_nHet$, $(CH_2)_nCONR_2$, $XCONR(CH_2)_nNR_2$, $N[(CH_2)_nXCOOR]CO(CH_2)_nAr$, $N[(CH_2)_nXR]CO(CH_2)_nAr$, $N[(CH_2)_nXR]CO(CH_2)_nXAr$, $N[(CH_2)_nXR]SO_2(CH_2)_nAr$, $N[(CH_2)_nNRCOOR]CO(CH_2)_nAr$, $N[(CH_2)_nNR_2]CO(CH_2)_nAr$, $N[(CH_2)_nNR_2]CO(CH_2)_nNRAr$, $N[(CH_2)_nNR_2]SO_2(CH_2)_nAr$, $N[(CH_2)_nXR]CO(CH_2)_nHet$, $N[(CH_2)_nXR]CO(CH_2)_nXHet$, $N[(CH_2)_nXR]SO_2(CH_2)_nHet$, $N[(CH_2)_nNRCOOR]CO(CH_2)_nHet$, $N[(CH_2)_nNR_2]CO(CH_2)_nHet$, $N[(CH_2)_nNR_2]CO(CH_2)_nNRHet$;
$R^2$, $R^3$ denotes H, A, Hal, OA, OR;
Y denotes H, A, Hal, OR;
A denotes Alkyl or Cycloalkyl, wherein one or more H-atoms can be replaced by Hal;
Hal denotes F, Cl, Br or I;
R denotes H or A, in the case of geminal groups R together also $—(CH_2)_5—$, $—(CH_2)_4—$ or $—(CH_2)_n—X—(CH_2)_n$, or $—(CH_2)_n—Z—(CH_2)_n$;
X denotes O, S, NA or NH;
Q denotes $CH_2—NH-A$, $CH_2—NH—C(O)R^1$, $CH_2—NH—SO_2R^1$;
Z denotes $CH_2$, X, $CHCONH_2$, $CH(CH_2)_nNRCOOR$, CHNRCOOR, NCHO, $CHCON(R)_2$, $CH(CH_2)_nCOOR$, NCOOR, $CH(CH_2)_nOH$, $N(CH_2)_nOH$, $CHNH_2$, $CH(CH_2)_nNR_2$, $CH(CH_2)_nNR_2$, $C(OH)R$, CHNCOR, NCOR, $N(CH_2)_nAr$, $N(CH_2)_nHet$, CHR, NR, $CH(CH_2)_nAr$, $CH(CH_2)_nHet$, $CH(CH_2)_nR$, $N(CH_2)_nCOOR$, $CH(CH_2)_nX(CH_2)_nAr$, $CH(CH_2)_nX(CH_2)_nHet$, $N(CH_2)_nCON(R)_2$, $NSO_2R$, $CHSO_2N(R)_2$, $XCONR(CH_2)_nN(R)_2$, $NCO(CH_2)_nAr$, $NCO(CH_2)_nXAr$, $NSO_2(CH_2)_nAr$, $NCO(CH_2)_nAr$, $NCO(CH_2)_nNRAr$, $NCO(CH_2)_nHet$, $NCO(CH_2)_nXHet$, $NSO_2(CH_2)_nHet$, $NCO(CH_2)_nNRHet$, $N(CH_2)_nNR_2CH$, $CHO(CH_2)_nN(R)_2$, $CHX(CH_2)_nN(R)_2$, or, $NCO(CH_2)_nNR_2$;
$R^6$ denotes unsubstituted Ar or Het which is substituted in at least one position by Hal, $NO_2$, CN, OR, A, $—(CY_2)_n—OR$, $—OCOR$, $—(CY_2)_n—CO_2R$, $—(CY_2)_n—CN$, $—NCOR$, $—COR$ or $—(CY_2)_n—NR_2$ or by Ar or Het which also may be substituted by Hal, $NO_2$, CN, A, OR, OCOR, COR, $NR_2$, $CF_3$, $OCF_3$, $OCH(CF_3)_2$,
$R^7$ denotes $(C=O)—R$, $(C=O)—NR_2$, $(C=O)—OR$, H or A;
Ar denotes a monocyclic or bicyclic, saturated, unsaturated or aromatic carbocyclic ring having 6 to 14 carbon atoms which may be unsubstituted which is substituted in at least one position by Hal, $NO_2$, CN, OR, A, $—(CY_2)_n—OR$, $—OCOR$, $—(CY_2)_n—CO_2R$, $—(CY_2)_n—CN$, $—NCOR$, $—COR$ or $—(CY_2)_n—NR_2$ or by Hal, $NO_2$, CN, A, OR, OCOR, COR, $NR_2$, $CF_3$, $OCF_3$, $OCH(CF_3)_2$;
Het denotes a monocyclic or bicyclic, saturated, unsaturated or aromatic heterocyclic ring having 1 to 4 N, O and/or S atoms which may be unsubstituted or which is substituted in at least one position by Hal, $NO_2$, CN, OR, A, $—(CY_2)_n—OR$, $—OCOR$, $—(CY_2)_nCO_2R$, $—(CY_2)_n—CN$, $—NCOR$, $—COR$ or $—(CY_2)_n—NR_2$ or by Hal, $NO_2$, CN, A, OR, OCOR, COR, $NR_2$, $CF_3$, $OCF_3$, $OCH(CF_3)_2$;
n denotes 0, 1, 2, 3, 4, 5, 6 or 7;
or a pharmaceutically acceptable tautomer or salt thereof, said process comprising:
reacting an aniline compound A and an aldehyde B

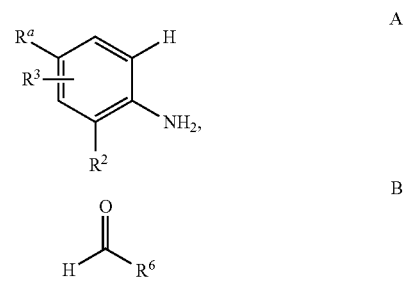

with a chiral dihydropyran methylamine compound C

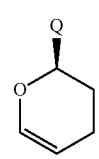

C in the presence of a suitable solvent and a protonic acid or Lewis acid wherein $R^1$ to $R^6$ and Q are as described above.

2. The process according to claim 1, wherein Q is —CH$_2$—NH(CO)R, —CH$_2$—NHSO$_2$R or CH$_2$NH-A.

3. The process according to claim 1, wherein Q is CH$_2$NH—CH$_3$, CH$_2$NH—C(O)NH(CH$_2$)$_2$N(CH$_3$)$_2$.

4. The process according to claim 1, wherein R$^6$ is an unsubstituted Ar.

5. The process according to claim 1, wherein R$^3$ is H.

6. The process according to claim 1, wherein R$^2$ is H.

7. The process according to claim 1, wherein R$^a$ is A.

8. The process according to claim 1, wherein R$^a$ is CF$_3$ and R$^7$ is H.

9. The process according to claim 1, wherein the protonic acid is trifluoroacetic acid.

10. The process according to claim 9, wherein the solvent is acetonitrile.

11. The process according to claim 1, wherein Q is —CH$_2$—NHCH$_3$, R$^a$ is Cl, R$^2$ is F, R$^3$ is H, R$^7$ is H and R$^6$ is unsubstituted Ar.

12. A process for the manufacture of enantiomerically enriched or pure compounds of formula C:

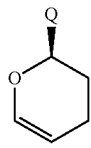

C wherein
Q denotes CH$_2$—NH-A, CH$_2$—NH—C(O)R$^1$, CH$_2$—NH—SO$_2$R$^1$,

R$^1$ denotes H, A, Ar, Het, Hal, —(CY$_2$)$_n$—SA, —(CY$_2$)$_n$—SCF$_3$, —(CY$_2$)$_n$—SCN, —(CY$_2$)$_n$—CF$_3$, —(CY$_2$)$_n$—OCF$_3$, R, cycloalkyl, —SCH$_3$, —SCN, —CF$_3$—OCF$_3$, —OA, —(CY$_2$)$_n$—OH, —(CY$_2$)$_n$—CO$_2$R, —(CY$_2$)$_n$—CN, —(CY$_2$)$_n$-Hal, —(CY$_2$)$_n$—NR$_2$, (CY$_2$)$_n$—OA, (CY$_2$)$_n$—OCOA, —SCF$_3$, (CY$_2$)$_n$—CONR$_2$, —(CY$_2$)$_n$—NHCOA, —(CY$_2$)$_n$—NHSO$_2$A, SF$_5$, Si(CH$_3$)$_3$, CO—(CY$_2$)$_n$—CH$_3$, —(CY$_2$)$_n$—N-Pyrrolidone, (CH$_2$)$_n$NRCOOR, NRCOOR, NCO, (CH$_2$)$_n$COOR, NCOOR, (CH$_2$)$_n$OH, NR(CH$_2$)$_n$NR$_2$, C(OH)R$_2$, NR(CH$_2$)$_n$OR, NCOR, (CH$_2$)$_n$Ar, (CH$_2$)$_n$Het, (CH$_2$)$_n$R, (CH$_2$)$_n$X(CH$_2$)$_n$Ar, (CH$_2$)$_n$X(CH$_2$)$_n$Het, (CH$_2$)$_n$CONR$_2$, XCONR(CH$_2$)$_n$NR$_2$, N[(CH$_2$)$_n$XCOOR]CO(CH$_2$)$_n$Ar, N[(CH$_2$)$_n$XR]CO(CH$_2$)$_n$Ar, N[(CH$_2$)$_n$XR]CO(CH$_2$)$_n$XAr, N[(CH$_2$)$_n$XR]SO$_2$(CH$_2$)$_n$Ar, N[(CH$_2$)$_n$NRCOOR]CO(CH$_2$)$_n$Ar, N[(CH$_2$)$_n$NR$_2$]CO(CH$_2$)$_n$Ar, N[(CH$_2$)$_n$NR$_2$]CO(CH$_2$)$_n$NRAr, N[(CH$_2$)$_n$NR$_2$]SO$_2$(CH$_2$)$_n$Ar, N[(CH$_2$)$_n$XR]CO(CH$_2$)$_n$Het, N[(CH$_2$)$_n$XR]CO(CH$_2$)$_n$XHet, N[(CH$_2$)$_n$XR]SO$_2$(CH$_2$)$_n$Het, N[(CH$_2$)$_n$NRCOOR]CO(CH$_2$)$_n$Het, N[(CH$_2$)$_n$NR$_2$]CO(CH$_2$)$_n$Het, N[(CH$_2$)$_n$NR$_2$]CO(CH$_2$)$_n$NRHet, Y denotes H, A, Hal, or OR, A denotes Alkyl or Cycloalkyl, wherein one or more H-atoms can be replaced by Hal Hal denotes F, Cl, Br or I, R denotes H or A, in the case of geminal groups R together also —(CH$_2$)$_5$—, —(CH$_2$)$_4$— or —(CH$_2$)$_n$—X—(CH$_2$)$_n$, or —(CH$_2$)$_n$—Z—(CH$_2$)$_n$, X denotes O, S, NH or NA, Q denotes CH$_2$—NH-A, CH$_2$—NH—C(O)R$^1$, CH$_2$—NH—SO$_2$R$^1$, Z denotes CH$_2$, X, CHCONH$_2$, CH(CH$_2$)$_n$NRCOOR, CHNRCOOR, NCHO, CHCON(R)$_2$, CH(CH$_2$)$_n$COOR, NCOOR, CH(CH$_2$)$_n$OH, N(CH$_2$)$_n$OH, CHNH$_2$, CH(CH$_2$)$_n$NR$_2$, CH(CH$_2$)$_n$NR$_2$, C(OH)R, CHNCOR, NCOR, N(CH$_2$)$_n$Ar, N(CH$_2$)$_n$Het, CHR, NR, CH(CH$_2$)$_n$Ar, CH(CH(CH$_2$)$_n$Het, CH(CH$_2$)$_n$R, N(CH$_2$)$_n$COOR, CH(CH$_2$)$_n$X(CH$_2$)$_n$Ar, CH(CH$_2$)$_n$X(CH$_2$)$_n$Het, N(CH$_2$)$_n$CON(R)$_2$, NSO$_2$R, CHSO$_2$N(R)$_2$, XCONR(CH$_2$)$_n$N(R)$_2$, NCO(CH$_2$)$_n$Ar, NCO(CH$_2$)$_n$XAr, NSO$_2$(CH$_2$)$_n$Ar, NCO(CH$_2$)$_n$Ar, NCO(CH$_2$)$_n$NRAr, NCO(CH$_2$)$_n$Het, NCO(CH$_2$)$_n$XHet, NSO$_2$(CH$_2$)$_n$Het, NCO(CH$_2$)$_n$NRHet, N(CH$_2$)$_n$NR$_2$CH, CHO(CH$_2$)$_n$N(R)$_2$, CHX(CH$_2$)$_n$N(R)$_2$, NCO(CH$_2$)$_n$NR$_2$, Ar denotes a monocyclic or bicyclic, saturated, unsaturated or aromatic carbocyclic ring having 6 to 14 carbon atoms which may be unsubstituted which is substituted in at least one position by Hal, NO$_2$, CN, OR, A, —(CY$_2$)$_n$—OR, —OCOR, —(CY$_2$)$_n$—CO$_2$R, —(CY$_2$)$_n$—CN, —NCOR, —COR or —(CY$_2$)$_n$—NR$_2$ or by Hal, NO$_2$, CN, A, OR, OCOR, COR, NR$_2$, CF$_3$, OCF$_3$, OCH(CF$_3$)$_2$, Het denotes a monocyclic or bicyclic, saturated, unsaturated or aromatic heterocyclic ring having 1 to 4 N, O and/or S atoms which may be unsubstituted or which is substituted in at least one position by Hal, NO$_2$, CN, OR, A, —(CY$_2$)$_n$—OR, —OCOR, —(CY$_2$)$_n$—CO$_2$R, —(CY$_2$)$_n$—CN, —NCOR, —COR or —(CY$_2$)$_n$—NR$_2$ or by Hal, NO$_2$, CN, A, OR, OCOR, COR, NR$_2$, CF$_3$, OCF$_3$, OCH(CF$_3$)$_2$, and n denotes 0, 1, 2, 3, 4, 5, 6 or 7, as well as their pharmaceutically acceptable tautomers and salts, said process comprising:

A)

treating the racemic compound C, wherein Q is CH$_2$NH$_2$ or CH$_2$NHA, with a chiral acid compound in a polar solvent to give enantiomerically enriched or pure dihydropyran methylamine salts;

and optionally using a base to obtain the free base from the dihydropyran methylamine salts;

or

B)

treating the racemic compound C, wherein Q is CH$_2$NH$_2$ or CH$_2$NHA, with a chiral acid compound in a polar solvent to give the enantiomerically enriched or pure dihydropyran methylamine salts;

optionally using a base to obtain the free base from the dihydropyran methylamine salts, and reacting the resulting compound with ClC(O)R$^1$ or ClSO$_2$R$^1$ in the presence of a non nucleophilic base in a polar solvent;

or

C)

treating the racemic compound C, wherein Q is CH$_2$NH$_2$ or CH$_2$NHA, with a chiral acid compound in a polar solvent to give the enantiomerically enriched or pure dihydropyran methylamine salts;

optionally using a base to obtain the free base from the dihydropyran methylamine salts, and reacting the resulting compound with a primary amine NH$_2$R$^1$ with CDI in a solvent.

13. The process according to claim 12 for the manufacture of enantiomerically enriched or pure compounds of formula C:

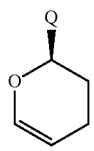

wherein Q denotes $CH_2$—NH-A, $CH_2$—NH—$C(O)R^1$, $CH_2$—NH—$SO_2R^1$, as well as their pharmaceutically acceptable tautomers and salts, said process comprising:

treating the racemic compound C, wherein Q is $CH_2NH_2$ or $CH_2NHA$, with a chiral acid compound in a polar solvent to give the enantiomerically enriched or pure dihydropyran methylamine salts;

optionally using a base to obtain the free base from the dihydropyran methylamine salts, and reacting the resulting compound with $ClC(O)R^1$ or $ClSO_2R^1$ in the presence of a non nucleophilic base in a polar solvent.

14. The process according to claim 12 for the manufacture of enantiomerically enriched or pure compounds of formula C:

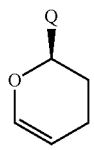

wherein Q denotes $CH_2$—NH-A, $CH_2$—NH—$C(O)R^1$, $CH_2$—NH—$SO_2R^1$, as well as their pharmaceutically acceptable tautomers and salts, said process comprising:

treating the racemic compound C, wherein Q is $CH_2NH_2$ or $CH_2NHA$, with a chiral acid compound in a polar solvent to give the enantiomerically enriched or pure dihydropyran methylamine salts;

optionally using a base to obtain the free base from the dihydropyran methylamine salts, and reacting the resulting compound with a primary amine $NH_2R^1$ with CDI in a solvent.

15. The process according to claim 12, wherein (a) Q is $CH_2NHMe$, the chiral acid compound is L-tosylproline, the polar solvent ethanol and the base is NaOH; or (b) Q is $CH_2NH_2$, and the chiral acid compound is (2R,3R)-(−)-Di-O-benzoyl tartaric acid.

16. The process according to claim 13, wherein $R^1$ is methyl, the chiral acid compound is L-tosylproline, the polar solvent ethanol, the base is NaOH and non nucleophilic base is triethylamine TEA.

17. The process according to claim 14, wherein $R^1$ is $CH_2$—$CH_2$—$N(CH_3)_2$, the chiral acid compound is L-tosylproline, the polar solvent ethanol, the base is NaOH, the coupling agent is 1,1'-carbonyldiimidazole and the solvent is $CH_2Cl_2$.

18. The process according to claim 1, wherein separation of the exo and endo compounds obtained, is achieved by recrystallization with chiral salts or acid.

19. The process according to claim 1, wherein compound C is obtained by

A)
treating the racemic compound C, wherein Q is $CH_2NH_2$ or $CH_2NHA$, with a chiral acid compound in a polar solvent to give enantiomerically enriched or pure dihydropyran methylamine salts; and optionally using a base to obtain the free base from the dihydropyran methylamine salts;

or

B)
treating the racemic compound C, wherein Q is $CH_2NH_2$ or $CH_2NHA$, with a chiral acid compound in a polar solvent to give the enantiomerically enriched or pure dihydropyran methylamine salts;

optionally using a base to obtain the free base from the dihydropyran methylamine salts, and reacting the resulting compound with $ClC(O)R^1$ or $ClSO_2R^1$ in the presence of a non nucleophilic base in a polar solvent;

or

C)
treating the racemic compound C, wherein Q is $CH_2NH_2$ or $CH_2NHA$, with a chiral acid compound in a polar solvent to give the enantiomerically enriched or pure dihydropyran methylamine salts;

optionally using a base to obtain the free base from the dihydropyran methylamine salts, and reacting the resulting compound with a primary amine $NH_2R^1$ with 1,1'-carbonyldiimidazole in a solvent.

20. The process according to claim 1, wherein said compound of formula I is a compound of formula $Ia_2$ or formula $Ib_2$

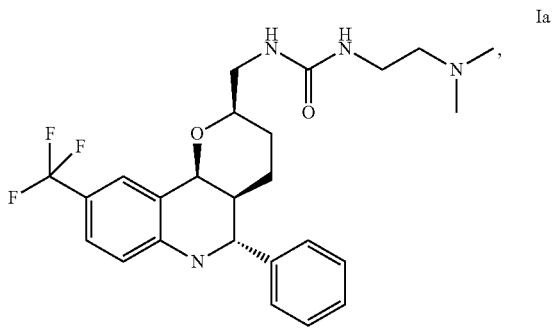

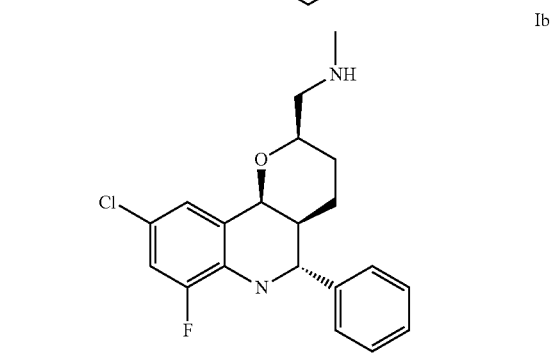

or a pharmaceutically acceptable tautomer or salt thereof.

21. The process according to claim 20, wherein enantiomerically enriched or pure compounds of formula $Ia_2$ are obtained by recrystallization with (2R,3R)-(−)-Di-O-benzoyl tartaric acid salt in EtOH.

22. The process according to claim 20, wherein enantiomerically enriched or pure compounds of formula $Ib_2$ are obtained by recrystallization with HCl in EtOH.

23. The process according to claim 12 for the manufacture of enantiomerically enriched or pure compounds of formula C:

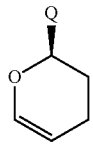

C wherein
- Q denotes $CH_2$—NH-A, $CH_2$—NH—$C(O)R^1$, $CH_2$—NH—$SO_2R^1$, as well as their pharmaceutically acceptable tautomers and salts, said process comprising:

treating the racemic compound C, wherein Q is $CH_2NH_2$ or $CH_2NHA$, with a chiral acid compound in a polar solvent to give enantiomerically enriched or pure dihydropyran methylamine salts;

and optionally using a base to obtain the free base from the dihydropyran methylamine salts.

* * * * *

UNITED STATES PATENT AND TRADEMARK OFFICE
CERTIFICATE OF CORRECTION

| | |
|---|---|
| PATENT NO. | : 8,278,454 B2 |
| APPLICATION NO. | : 12/808819 |
| DATED | : October 2, 2012 |
| INVENTOR(S) | : Ulrich Emde et al. |

It is certified that error appears in the above-identified patent and that said Letters Patent is hereby corrected as shown below:

Column 36, line 65, reads "of a suitable solvent", should read --of a solvent--.

Signed and Sealed this
Twenty-second Day of January, 2013

David J. Kappos
*Director of the United States Patent and Trademark Office*